United States Patent
Laali

(10) Patent No.: US 9,284,336 B1
(45) Date of Patent: Mar. 15, 2016

(54) SYNTHESIS OF 4-(PENTAFLUOROSULFANYL)-BENZENEDIAZONIUM TETRAFLUOROBORATE AND ANALOGS

(71) Applicant: Kenneth K. Laali, Jacksonville, FL (US)

(72) Inventor: Kenneth K. Laali, Jacksonville, FL (US)

(73) Assignee: University of North Florida, Jacksonville, FL (US)

( * ) Notice: Subject to any disclaimer, the term of this patent is extended or adjusted under 35 U.S.C. 154(b) by 0 days.

(21) Appl. No.: 14/966,769

(22) Filed: Dec. 11, 2015

Related U.S. Application Data

(62) Division of application No. 14/465,257, filed on Aug. 21, 2014, now Pat. No. 9,238,660.

(51) Int. Cl.
| | |
|---|---|
| *C07C 323/31* | (2006.01) |
| *C07F 5/02* | (2006.01) |
| *C07C 67/00* | (2006.01) |
| *C07C 381/00* | (2006.01) |
| *B01J 31/02* | (2006.01) |
| *B01J 31/18* | (2006.01) |

(52) U.S. Cl.
CPC .............. *C07F 5/022* (2013.01); *B01J 31/0204* (2013.01); *B01J 31/0275* (2013.01); *B01J 31/1805* (2013.01); *C07C 67/00* (2013.01); *C07C 323/31* (2013.01); *C07C 381/00* (2013.01); *B01J 2231/4283* (2013.01)

(58) Field of Classification Search
CPC ...................................................... C07C 323/31
See application file for complete search history.

(56) References Cited

FOREIGN PATENT DOCUMENTS

WO      WO2005123749      * 12/2005      ............... C07F 5/02

* cited by examiner

*Primary Examiner* — Robert Havlin
(74) *Attorney, Agent, or Firm* — Robert J. Varkonyi; Smith & Hopen, P.A.

(57) ABSTRACT

4-(pentafluorosulfanyl)benzenediazonium tetrafluoroborate salt was synthesized and isolated. The pentafluorosulfanyl salt was examined in a wide assortment of reactions to form novel $SF_5$-bearing alkenes, alkynes, and biaryl derivatives using Heck-Matsuda, Sonogashira, and Suzuki coupling protocols. Dediazoniation of the salt furnished the corresponding p-$SF_5$—$C_6H_4X$, $C_6H_4OS(O)(CF_3)$=$NSO_2CF_3$, and p-$SF_5$—$C_6H_4$—$NTf_2$ derivatives. The azide derivative p-$SF_5$—$C_6H_4N_3$ entered into click chemistry with phenylacetylenes to furnish the corresponding triazoles. Various $SF_5$-bearing alkenes were synthesized by coupling reactions using a metal catalyst. Fluorodediazoniation selectively furnished the fluoro derivative p-$SF_5$—$C_6H_4F$. Homolytic dediazoniation gave the unsymmetrical biaryls, thus demonstrating the broad utility of pentafluorosulfanyl diazonium salts as building blocks of SF5-aromatics that are in high demand in many branches of chemistry including biomedicine and materials chemistry.

8 Claims, 9 Drawing Sheets

SYNTHESIS OF 4-(PENTAFLUOROSULFANYL)-BENZENEDIAZONIUM TETRAFLUOROBORATE AND ANALOGS

CROSS-REFERENCE TO RELATED APPLICATIONS

This application is a divisional application of and claims priority to U.S. patent application Ser. No. 14/465,257, entitled "Synthesis of 4-(pentafluorosulfanyl)benzenediazonium tetrafluoroborate and Analogs and Their Application for the Preparation of SF$_5$-aromatics", filed on Aug. 21, 2014, the contents of which are herein incorporated by reference.

FIELD OF INVENTION

This invention relates to synthesis of specialty chemicals. More specifically, the present invention provides synthetic methods for the preparation of SF5-aromatic diazonium salts and the application of such salts as building blocks for the preparation of a wide variety of SF5-aromatics.

BACKGROUND OF THE INVENTION

The presence of the pentafluorosulfanyl (SF$_5$) group imparts a number of favorable physical and chemical characteristics including thermal, hydrolytic, and chemical stability, high density, high electronegativity, and high lipophilicity. These favorable characteristics have prompted a high degree of interest in SF$_5$-organics for potential applications in the biomedical and materials fields (Altomonte & Zanda, *J. Fluorine Chem.* 2012, 143, 57-93). As such, pentafluorosulfanyl-substituted compounds are undergoing extensive studies for use as high performance polymers, liquid crystals, pharmaceuticals and pesticides (Thayer, *Chem. Eng. News* 2006, 84:27-32).

As a substituent on an aromatic ring the SF$_5$ group acts as a sterically demanding, strongly electron-withdrawing/deactivating group. A major drawback in the development of synthetic chemistry of SF$_5$-arenes has been the lack of practical methods that avoid the use of exotic/hazardous reagents and harsh conditions. In early pioneering studies Sheppard synthesized the parent (pentafluorosulfanyl)benzene and its p-nitro derivative in modest yields by reacting the corresponding aryl disulfides or aryl sulfur trifluorides with excess AgF$_2$ in chlorofluorocarbon solvent at elevated temperatures in a copper reactor (Sheppard, *J. Am. Chem. Soc.* 1962, 84, 3064-3072). This method was later employed by Thrasher et al. (Sipyagin, et al., *J. Fluorine Chem.* 2001, 112, 287-295; Sipyagin, et al., *J. Fluorine Chem.* 2004, 125, 1305-1316) to prepare various substituted derivatives of PhSF$_5$ in modest overall yields and many side products. Subsequent methods reported from other laboratories involved elemental fluorination starting with the corresponding bisnitrophenyl disulfide, (Bowden, et al., *Tetrahedron* 2000, 56, 3393-3408; Kirsch & Hahn, *Eur. J. Org. Chem.* 2005, 3095-3100; Kirsch & Hahn, *Eur. J. Org. Chem.* 2006, 1125-1131; Kirsch, et al., *Angew. Chem.* 1999, 111, 2174; Kirsch, et al., *Angew. Chem. Int. Ed.* 1999, 38, 1989-1992) and high pressure reactions with gaseous SF$_5$ halides (Sergeeva & Dolbier Jr, *Org. Lett.* 2004, 6, 2417-2419; Winter & Gard, *J. Fluorine Chem.* 2004, 125, 549-552). The 3-nitro derivative is accessible by direct electrophilic nitration of PhSF$_5$ (Sheppard, *J. Am. Chem. Soc.* 1962, 84, 3064-3072; Bowden, et al., *Tetrahedron* 2000, 56, 3393-3408; Kirsch & Hahn, *Eur. J. Org. Chem.* 2005, 3095-3100; Kirsch & Hahn, *Eur. J. Org. Chem.* 2006, 1125-1131; Kirsch, et al., *Angew. Chem.* 1999, 111, 2174; Kirsch, et al., *Angew. Chem. Int. Ed.* 1999, 38, 1989-1992; Sergeeva & Dolbier Jr, *Org. Lett.* 2004, 6, 2417-2419). A recent method reported by Umemoto et al. (Umemoto, et al., *Beilstein J. Org. Chem.* 2012, 8, 461-471) involves synthesis of ArSF$_4$Cl from ArSSAr or ArSH by reaction with Cl$_2$/KF or CsF and subsequent transformation to ArSF$_5$ by ZnF$_2$/heat.

The strongly deactivating effect of SF$_5$ group makes PhSF$_5$ amenable to S$_N$Ar chemistry notably with alkoxides and thiolate, (Beier, et al., *Org. Lett.* 2011, 13, 1466-1469) and by vicarious nucleophilic substitution of hydrogen (Beier, et al., *J. Org. Chem.* 2011, 76, 4781-4786; Iakobson, et al., *Synlett* 2013, 24, 855-859; Vida & Beier, *J. Fluorine Chem.* 2012, 143, 130-134). By contrast, the S$_E$Ar chemistry of SF$_5$-aromatics has remained under-developed. In early work by Bowden (Bowden, et al., *Tetrahedron* 2000, 56, 3393-3408) the 3-iodo and 4-iodo derivatives were synthesized by in-situ diazotization and reaction with KI, and were shown to enter into cross coupling reactions in representative cases. Formation of an SF$_5$-based azo-dye by in-situ diazotization and coupling to PhNMe$_2$ was reported by Kirsch and Hahn (Kirsch & Hahn, *Eur. J. Org. Chem.* 2006, 1125-1131). However, the F$_5$S—C$_6$H$_4$N$_2$$^+$ salt was never isolated in earlier studies to allow its use as a key building block for the synthesis of other SF$_5$-aromatics using diazonium ion chemistry.

The commercial availability of parent PhSF$_5$ and a few other derivatives, notably the p-Me, the p-NH$_2$, and the m- and p-NO$_2$ derivatives has remedied some of the preparatory problems. However, there are only a few readily available pentafluorosulfanyl compounds, significantly limiting the use of pentafluorosulfanyl-based synthesis. Much of the current technology focuses on synthetic methods that use of exotic and/or hazardous reagents and harsh conditions. As such, what is required is a readily available starting pentafluorosulfanyl-substituted compound for use in pentafluorosulfanyl-based synthesis.

SUMMARY OF THE INVENTION

In relation to our continuing interest in diazonium ion chemistry and dediazoniation, (Laali, et al., *Helv. Chim. Acta* 1983, 66, 1737-1747; Laali & Gettwert, *J. Fluorine Chem.* 2001, 107, 31-34; Hubbard, et al., *J. Org. Chem.* 2008, 73, 316-319; Laali, et al., *J. Org. Chem.* 2007, 72, 6758-6762) and in the application of ArN$_2$$^+$ in ligand coupling reactions, (Kalkhambekar & Laali, *Tetrahedron Lett.* 2011, 52, 1733-1737) a synthetic method and isolation of SF5-substituted aromatic diazonium salts, such as 4-(pentafluorosulfanyl benzenediazonium tetrafluoroborate, was developed. To synthesize the SF$_5$-bearing diazonium salt, an SF5-aromatic reactant was treated with tert-butyl nitrite and boron trifluoride etherate in an anhydrous solvent below 0° C. to form an SF$_5$-bearing aromatic diazonium salt which was then isolated as stable compound.

The SF5-aromatic reactant is optionally 4-(pentafluorosulphanyl)-aniline, 3-(pentafluorosulphanyl)-aniline, or isomeric SF$_5$-substituted methyl anilines. In addition anilines derived from SF5-biphenyl and 1,1'-bis-SF5-biphenyl can serve as precursors to other SF5-bearing aromatic diazonium salts.

Useful reaction solvents include dichloromethane, dichloroethane, chloroform, diethyl ether, or combinations thereof.

Useful boron trifluoride sources include boron trifluoride diethyl etherate, boron trifluoride tert-butyl methyl etherate, boron trifluoride dibutyl etherate, and boron trifluoride acetonitrile complex. Diazotization employing tert-butyl nitrite/ BF$_3$.etherate are carried out in CH$_2$Cl$_2$ at about −10° C. to about 0° C. Nonlimiting examples include −10° C., −9° C., −8° C., −7° C., −6° C., −5° C., −4° C., −3° C., −2° C., −1° C., or 0° C. Other means of diazotization of the aniline compound are typically carried out at 0° C. (ice bath).

The resulting SF5-bearing aromatic diazonium salt was then purified by treating with mixed solvents, for example by dissolving in minimal amount of acetonitrile and then adding diethyl ether or dibutyl ether until the salt precipitated out of solution.

The SF5-aromatic diazonium salt resulting from the methods described herein have a general formula shown below, with $R_1$ and $R_2$ (typically methyl or other alkyl groups) and $X=BF_4$,

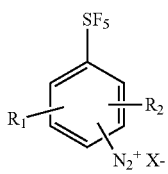

Some exemplary aromatic sulfofluorinated salts include 4-(pentafluorosulphanyl)-phenyl-diazonium tetrafluoroborate, 3-(pentafluorosulphanyl)-phenyl-diazonium tetrafluoroborate, and 5-(pentafluorosulphanyl)-phenyl-1,3-diazonium tetrafluoroborate.

In addition anilines derived from SF5-biphenyl via Suzuki coupling; and 1,1'-bis-SF5-biphenyl are useful precursors to other SF5-bearing aromatic diazonium salts, whereas the 3,5-dinitro-pentafluorosulfanyl-benzene accessible by di-nitration of SF5-benzene (T. Okazaki, K. K. Laali *Journal Fluorine Chemistry* 2014, 165, 96-100) are logical precursors to the bis-diazonium salt for further elaboration.

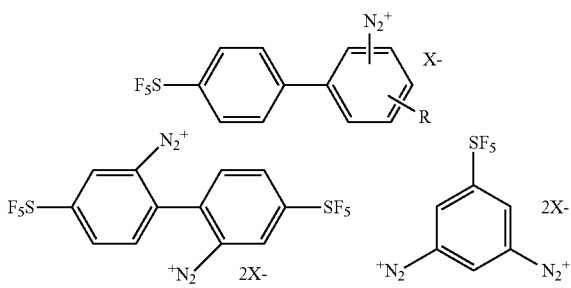

The utility of the $SF_5$-aromatic diazonium salt, such as 4-(pentafluorosulfanyl)phenyl diazonium tetrafluoroborate (1), as a versatile building block for the synthesis of a host of aromatic $SF_5$ compounds by cross coupling, azo-coupling, homocoupling, dediazoniation, and click chemistry has been demonstrated. Significantly, the present approach has the potential to significantly expand the library of $SF_5$-aromatics for further applications in the biomedical and materials fields.

The SF5-aromatic diazonium salt was subjected to reactions with a palladium catalyst in organic solvent in the presence of an alkene, such as substituted styrenes, methyl acrylate, and ethylene with a perfluorinated chain, or an alkyne, such as phenylacetylenes, in alcoholic solvents such as methanol and ethanol, to form coupling products. The diazonium salt also reacts with trimethylsilyl azide ($TMSN_3$), iodotrimethylsilane (TMSI), ammonium thiocyanate ($NH_4SCN$), trimethylsilyl chloride (TMSCl), in ionic liquid solvents such as 1-butyl-3-methylimidazolium bis(trifluoromethylsulfonyl)imide, 1-butyl-3-methylimidazolium tetrafluoroborate, and 1-butyl-3-methylimidazolium hexafluorophosphate to form the corresponding azides, halides, thiocyanates, or cyano derivatives.

In specific variations of the invention, the SF5-aromatic diazonium salt is reacted with trimethylsilyl azide in 1-butyl-3-methylimidazolium tetrafluoroborate as solvent, and the resulting SF5-aromatic azide is further reacted with a metal alloy catalyst in an organic solvent to form triazole derivatives. In specific cases the metal catalyst is a copper-zinc nanopowder and the organic solvent is dimethylformamide.

In some embodiments, the $SF_5$-aromatic diazonium salt is reacted with reactive aromatic compounds such as di- and trimethoxybenzenes to form azo-dyes.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
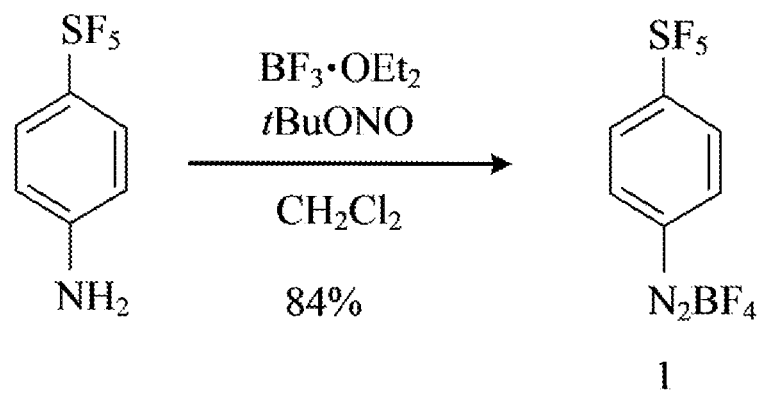
FIG. 1 is a reaction scheme showing the synthesis of diazonium salts from 4-(pentafluorsulfanyl)-aniline.

The reagent 4-(pentafluorosulfanyl)benzenediazonium tetrafluoroborate (1) was synthesized and isolated as a stable salt; and its application in a wide assortment of transformations was investigated. A series of novel $SF_5$-bearing alkenes, alkynes, and biaryl derivatives were synthesized by employing Heck-Matsuda, Sonogashira, and Suzuki coupling protocols. Dediazoniation with TMSX (X=Hal; $N_3$; and CN) and $NH_4SCN$ in [BMIM][BF$_4$] as solvent furnished the corresponding p-SF$_5$—C$_6$H$_4$X derivatives. The azide derivative p-SF5-C$_6$H$_4$N$_3$ entered into click chemistry with phenylacetylenes to furnish the corresponding triazoles. The 4,4'-bis(pentafluorosulfanyl)biphenyl was synthesized by homocoupling using Pd(OAc)$_2$. The corresponding azo compounds were obtained through azo-coupling with reactive aromatic nucleophiles (1,3-dimethoxybenzene, 1,3,5-trimethoxybenzene, 1,2,4-trimethoxybenzene, aniline and phenol). Fluorodediazoniation in [BMIM][PF$_6$] and [BMIM][BF$_4$] selectively furnished the fluoro derivative p-SF$_5$—C$_6$H$_4$F. Dediazoniation in [BMIM][NTf$_2$] gave p-SF$_5$—C$_6$H$_4$OS(O)(CF$_3$)=NSO$_2$CF$_3$ as the major and p-SF$_5$—C$_6$H$_4$-NTf$_2$ as the minor products. Homolytic dediazoniation in MeCN/NaI gave the unsymmetrical biaryls p-SF$_5$—C$_6$H$_4$—Ar (ArH=mesitylene and p-xylene) along with p-SF$_5$—C$_6$H$_4$I. Analysis of the dediazoniation product mixtures indicated that dediazoniation of p-SF SF$_5$—C$_6$H$_4$N$_2^+$ BF$_4^-$ in low nucleophilicity, highly ionizing, solvents (TfOH, TFE, HFIP, TFAH) is mainly heterolytic, while in MeOH it is mainly homolytic.

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical.

As used herein, "aromatic" means compounds such as benzene and its derivatives having a planar 6-pi electron periphery.

As used herein, "alkene" means a hydrocarbon having at least one double bond, i.e. that the carbon chain is unsaturated.

As used herein, "aryl" means aromatic carbocyclic radical with six or more carbon atoms. The aryl may be monocyclic like phenyl or bicyclic like naphthyl. These carbocyclic radicals may carry one or more substituents which may be the same or different. These substituents include alkyl-, aryl-, aralkyl-, hydroxy-, hydroxyalkyl-, alkoxy-, aryloxy-, aralkoxy-, carboxy-, acyl-, aroyl-, halo-, nitro-cyano-, carboxy-, alkoxycarbonyl-, aryloxycarbonyl-, aralkoxycarbonyl-, acylamino-, aroylamino-, alkylsulfonyl-, arylsulfonyl-, alkylsulfinyl-, arylsulfinyl-, alkylthio-, arylthio- and aralkylthio groups(s).

As used herein, "hetero-aryl" means an aryl moiety, including without limiting the scope of the invention monocyclic and bicyclic aryls, which contains a heteroatom in the aryl moiety. Non-limiting examples of heteroatoms include nitrogen, oxygen or sulfur. The hetero-aryl may also be substituted by one or more aryl group substituents, such as the substituents described in the definition of aryls.

As used herein, "hetero-biaryl" means a hetero-aryl, as defined herein, joined by a single bond to a phenyl or aryl (Altomonte & Zanda, Synthetic chemistry and biological activity of pentafluorosulphanyl (SF5) organic molecules. J. Fluor. Chem. Nov. 2012; 143:57-93).

Example 1

4-(Pentafluorosulfanyl)phenyldiazonium tetrafluoroborate (1) was synthesized and isolated for use as a starting material for subsequent reactions. In early trials diazonium salt 1 could not be isolated by employing classical diazotization methods for aromatic amine (as in Starkey, *Org. Synth.* 1939, 19, 40). Diazotization could be affected by using NaNO$_2$/HBF$_4$ but the resulting diazonium salt would not precipitate out of solution following dilution of the aqueous solution with ether, dichloromethane, or hexane. "Dry" diazotization as previously reported by Doyle and Bryker (Doyle & Bryker, *J. Org. Chem.* 1979, 44, 1572-1574), using tent-butyl nitrite/BF$_3$.OEt$_2$ in cold CH$_2$Cl$_2$, as seen in FIG. 1, successfully afforded the diazonium salt as a colorless precipitate which, following purification with MeCN/ether, furnished the diazonium salt as a pale-yellow solid. Tetrafluoroborate salt 1 is highly stable and can be stored at room temperature for extended periods. The $v_{N-N}$ frequency of 1 was observed at 2309 cm$^{-1}$, consistent with the extreme deactivating inductive effect of the p-SF5 group. For comparison purposes it is instructive to note that the $v_{N-N}$ frequency for 4-NO$_2$C$_6$H$_4$N$_2^+$ is at 2280 cm$^{-1}$ (Tabei & Ito, *Bull. Chem. Soc. Jpn.* 1968, 41, 514-515). Attempts were made to obtain an X-ray structure for the diazonium salt but the crystals did not diffract well enough to render viable crystallographic data.

Example 2

The p-SF5 substituted diazonium salt, prepared as described in Example 1, entered into Heck-Matsuda coupling reaction with styrene and 4-substituted styrenes in the presence of catalytic Pd(OAc)$_2$ in ethanol to give corresponding 4'-substituted 4-(pentafluorosulfanyl) stilbenes 2a-e, as seen in Table 1. Heck coupling in 1-butyl-3-methylimidazolium tetrafluoroborate [BMIM][BF$_4$] ionic liquid (R. G. Kalkhambekar, K. K. Laali, *Tetrahedron Lett.* 2011, 52, 1733-1737) instead of EtOH resulted in lower isolated yields due to the increased formation of homo-coupling products (styrene dimer and oligomers) that could not be effectively separated from the desired stilbene.

TABLE 1

Heck-Matsuda arylation with styrenes.

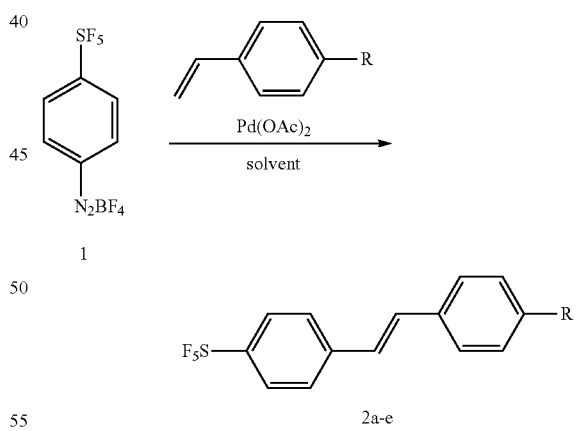

| R | Solvent | Temp [° C.] | Time [h] | Yield[a] [%] |
|---|---|---|---|---|
| H (2a) | 95% EtOH | 70 | 15 | 77 |
| H (2b) | [BMIM][BF$_4$] | r.t. | 22 | 23 |
| F (13c) | 95% EtOH | 70 | 5 | 77 |
| CH$_3$ (2c) | 95% EtOH | 70 | 5 | 82 |
| Cl (2d) | 95% EtOH | r.t. | 24 | 65 |
| CH$_3$COO (2e) | 95% EtOH | r.t. | 14 | 64 |

[a]Isolated yield after SiO$_2$ column chromatography.

Figure 2:
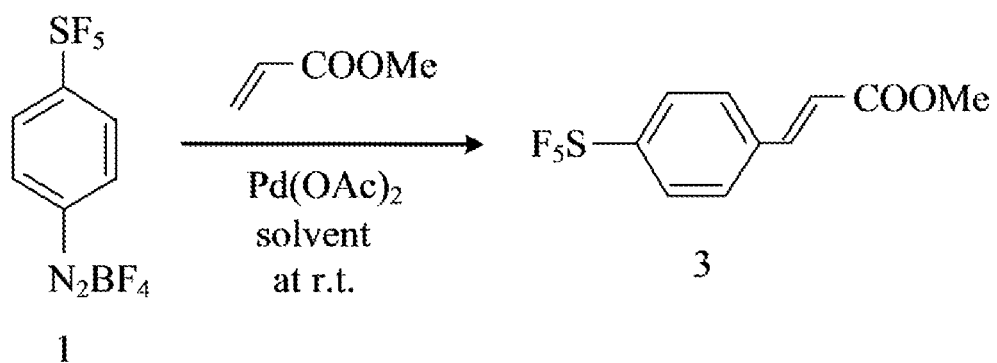
FIG. 2 is a reaction scheme showing Heck coupling of diazonium salts with methyl acrylate.

Diazonium salt 1 reacted with methyl acrylate in the presence of Pd(OAc)$_2$ in 95% EtOH to give methyl trans-3-[4-(pentafluorosulfanyl)phenyl]prop-2-enoate 3 in 85% isolated yield with no cis isomer being observed, as seen in FIG. 2.

The coupling reaction with methyl methacrylate gave a mixture of two isomeric products namely methyl 2-methyl-3-[4-(pentafluorosulfanyl)phenyl]prop-2-enoate 4 and methyl 2-{[4-(pentafluorosulfanyl)phenyl]methyl}prop-2-enoate 5 in a 1:2 ratio in 78% isolated yield, as seen in Table 2. Optimal yields were obtained after 18 h at room temp. in EtOH. A near quantitative yield was reached at room temp. when using [BMIM][BF$_4$] as the solvent although increased formation of isomer 5 was also noted with these reaction conditions.

TABLE 2

Heck-Matsuda arylation with methyl methacrylate.

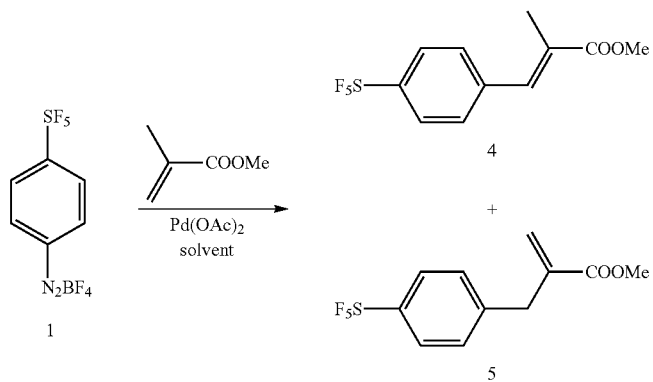

| Solvent | Temp [° C.] | Time [h] | Ratio of 4/5 | Yield[a] [%] |
|---|---|---|---|---|
| 95% EtOH | 70 | 4 | 1:2 | 77 |
| 95% EtOH | 70 | 2 | 1:2 | 23 |
| 95% EtOH | r.t. | 18 | 1:2 | 77 |
| [BMIM][BF$_4$] | r.t. | 16 | 1:3 | 82 |

[a]Combined yield after SiO$_2$ column chromatography.

In representative cases, diazonium salt 1 entered into coupling with fluorous olefins to give novel polyfluorinated adducts 7a and 7b, seen in Table 3.

TABLE 3

Heck arylation with fluoroalkenes.

| R | Solvent | Temp [° C.] | Time [h] | Yield[a] [%] |
|---|---|---|---|---|
| (CF$_2$)$_3$CF$_3$ (7a) | 95% EtOH | r.t. | 24 | 81 |
| (CF$_2$)$_3$CF$_3$ (7a) | 95% EtOH | r.t. | 20 | 69 |
| (CF$_2$)$_3$CF$_3$ (7a) | [BMIM][BF$_4$] | r.t. | 17 | 0[b] |

TABLE 3-continued

Heck arylation with fluoroalkenes.

| R | Solvent | Temp [° C.] | Time [h] | Yield[a] [%] |
|---|---|---|---|---|
| (CF$_2$)$_3$CF$_3$ (7a) | 95% EtOH | r.t. | 24 | 81 |
| (CF$_2$)$_3$CF$_3$ (7a) | [BMIM][BF$_4$] | 70 | 20 | 13[b] |

TABLE 3-continued

Heck arylation with fluoroalkenes.

| R | Solvent | Temp [° C.] | Time [h] | Yield[a] [%] |
|---|---|---|---|---|
| (CF$_2$)$_3$CF$_3$ (7a) | 95% EtOH | r.t. | 24 | 81 |
| (CF$_2$)$_5$CF$_3$ (7b) | 95% EtOH | r.t. | 16 | 83 |

[a]Isolated yield after SiO$_2$ column chromatography.
[b]After extraction with hexane.

To further expand the scope of the Heck-Matsuda reaction, coupling of 1 with camphene, norbornene, and trans-stilbene was also investigated, as see in Table 4. Coupling with camphene afforded 9 in respectable isolated yield. Coupling with trans-stilbene gave an inseparable isomeric mixture of 11 and 12 (as indicated by NMR) (Cacchi, et al., *Org. Lett.* 2008, 10, 1597-1600).

TABLE 4

Heck arylation with reactive alkenes.

| Alkene | Solvent | Temp. | Time | Product (yield)[a] |
|---|---|---|---|---|
| (2,3-dimethyl-3-methylenebicyclo[2.2.1]heptane) | 95% EtOH | r.t. | 16 h | 9 (89%) |
| (norbornene) | 95% EtOH | 70° C. | 1.5 h | 10 (0%) |
| (trans-stilbene) | 95% EtOH | 70° C. | 40 min | 11 + 12 (45% by NMR) |

[a]Isolated yield after SiO$_2$ column chromatography.

Example 3

The diazonium salt formed in Example 1 was subjected to Suzuki coupling. Diazonium salt 1 was allowed to react with Ar—B(OH)$_2$ under standard Suzuki coupling conditions. These reactions yielded corresponding biaryl derivatives 13a-c in isolated yields ranging from 27-59%, as seen in Table 5.

TABLE 5

Suzuki-coupling with 1.

SF$_5$-C$_6$H$_4$-N$_2$BF$_4$ (1) + R-C$_6$H$_4$-B(OH)$_2$ →[Pd(OAc)$_2$, Na$_2$CO$_3$, 95% EtOH] F$_5$S-C$_6$H$_4$-C$_6$H$_4$-R (13a-c)

| R | Temp [°C] | Time [h] | Yield$^a$ [%] |
|---|---|---|---|
| 4-CF$_3$ (13a) | 70 | 3 | 27 |
| 3,4,5-F$_3$ (13b) | r.t. | 24 | 44 |
| 3,5-Me$_2$ (13c) | r.t. | 20 | 59 |

$^a$Isolated yield after SiO$_2$ column chromatrography.

Figure 3:
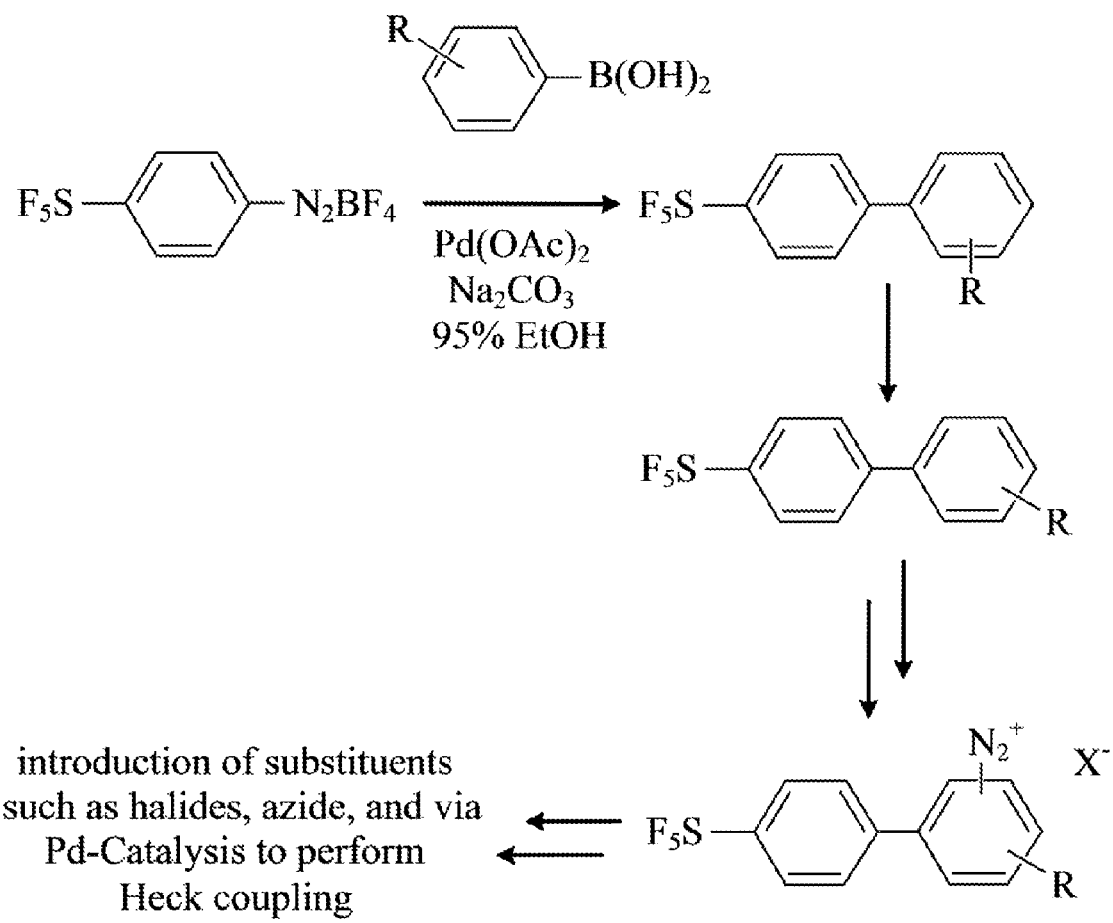
FIG. 3 is a reaction scheme showing the synthesis of $SF_5$-substituted biphenyl diazonium salts as starting point for the synthesis of derivatives of SF5-biphenyl

The biphenyl-derivatives synthesized by Suzuki coupling may be used as precursors to form bis-diazonium salts. The transformation of the precursors to diazonium salts are performed via nitration, reduction to amine and diazotization, as seen in FIG. 3. Moreover, the compounds derived in the present example can be further functionalized, extending the scope of the derivatives that can be synthesized.

Example 4

Figure 4:
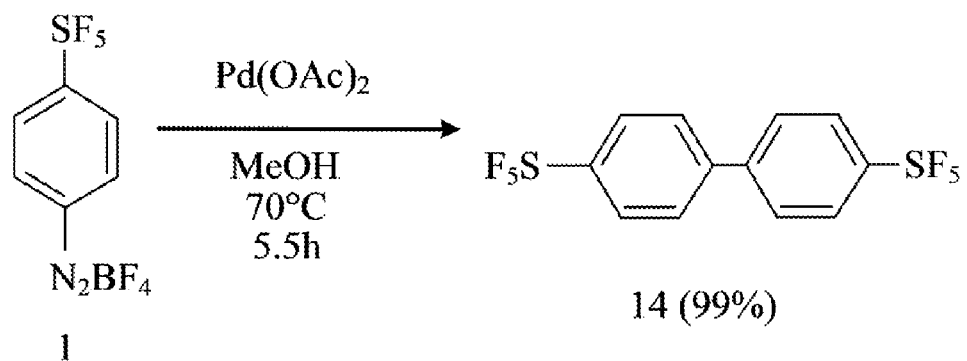
FIG. 4 is a reaction scheme showing biaryl synthesis through homocoupling chemistry of SF5-diazonium salts.

Biaryls were synthesized from the diazonium salt prepared in Example 1. 1,4'-bis(pentafluorsulfanyl)biphenyl (14) was successfully obtained in near quantitative yield by homocoupling using Pd(OAc)$_2$ in MeOH solvent, as seen in FIG. 4. It is worth noting that Kirsch and Hahn accidentally obtained compound 14 in 6% yield while attempting to metalate p-BrC$_6$H$_4$SF$_5$ with nBuLi/THF (Kirsch, et al., *Angew. Chem.* 1999, 111, 2174; Kirsch, et al., *Angew. Chem. Int. Ed.* 1999, 38, 1989-1992). The X-ray structure of compound 14 was determined, confirming that the formed compound was a biaryl species (not shown).

Figure 5:
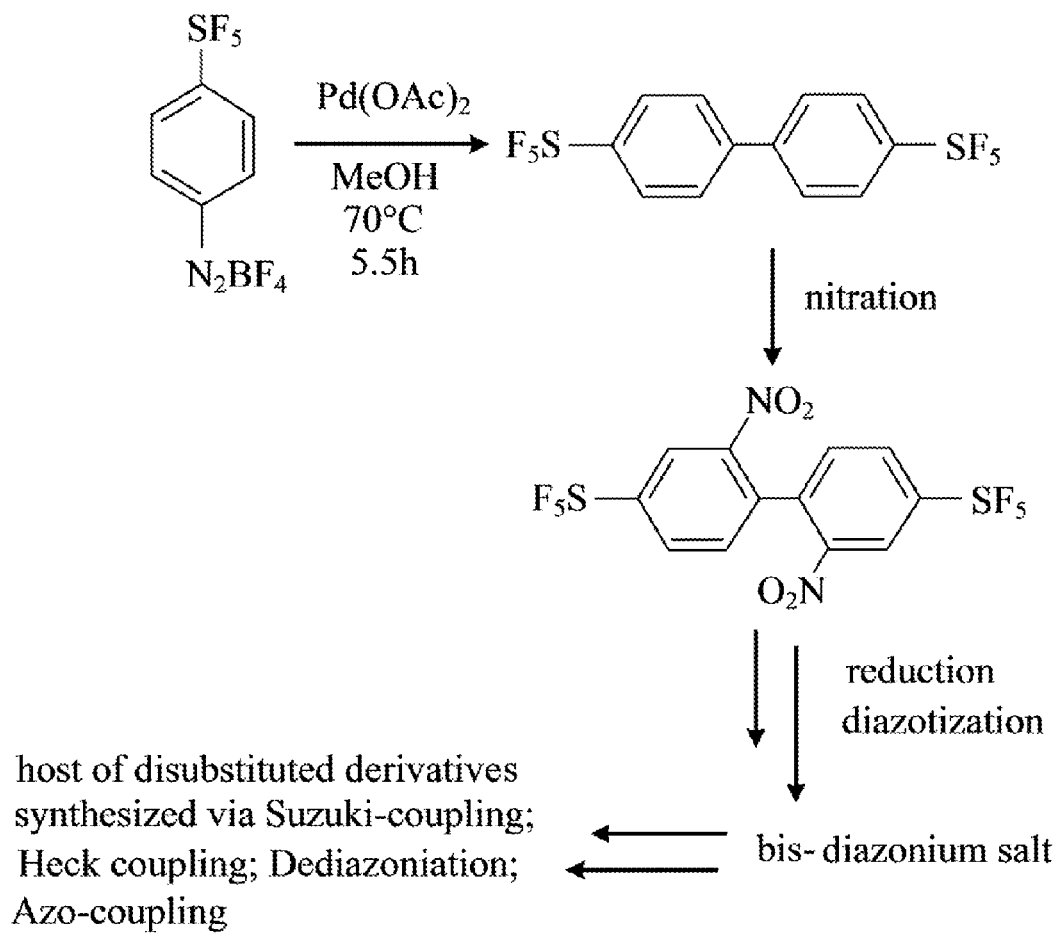
FIG. 5 is a reaction scheme showing bis-diazonium synthesis using nitration, nitro-reduction, and diazotization.

Bis-diazonium salt can be synthesized and either isolated or generated in-situ using compound 14 that could then serve as a starting point to introduce two substituents into the biphenyl structure, as seen in FIG. 5.

Example 5

Bis-diazonium groups can be added to a SF$_5$-bearing benzene. A dinitro-derivative benzene was synthesized using a two-step reaction scheme.

PhSF$_5$ 15 reacts with NO$_2$+BF$_4$−/TfOH in CH$_2$Cl$_2$ at room temperature to give 1-nitro-3-(pentafluorosulfanyl)benzene 16 in near quantitative yield, as seen in Table 6.

TABLE 6

Nitration of PhSF5 with nitronium tetrafluoroborate under various conditions.

15 (PhSF$_5$) →[NO$_2$BF$_4$] 16 (3-NO$_2$-C$_6$H$_4$-SF$_5$)

| Solvent | NO$_2$BF$_4$ | Temp | Time | 2 yield (isolated, %)$^a$ |
|---|---|---|---|---|
| CH$_2$Cl$_2$ | 1.7 eq | rt | 1 day | 61$^b$ |
| CH$_2$Cl$_2$ | 1.1 eq | rt | 18 hours | 44$^b$ |
| TfOH/CH$_2$Cl$_2$ | 1.1 eq | rt | 1 day | 100$^c$ |
| TfOH (neat) | 1.5 eq | rt | | 66$^b$ |
| CH$_2$Cl$_2$ | 8.3 eq | reflux for 3 hours, rt for 4 days; 40° C. for 5 hours; | | 83$^c$ |
| TfOH (neat) | 15 eq | 70° C. for 14 hours | | |

$^a$Isolated yield after SiO$_2$ column chromatography.
$^b$Traces of the p-nitro isomer was detected.
$^c$Crude product was found to be pure except for a trace of the p-nitro isomer.

Figure 6:
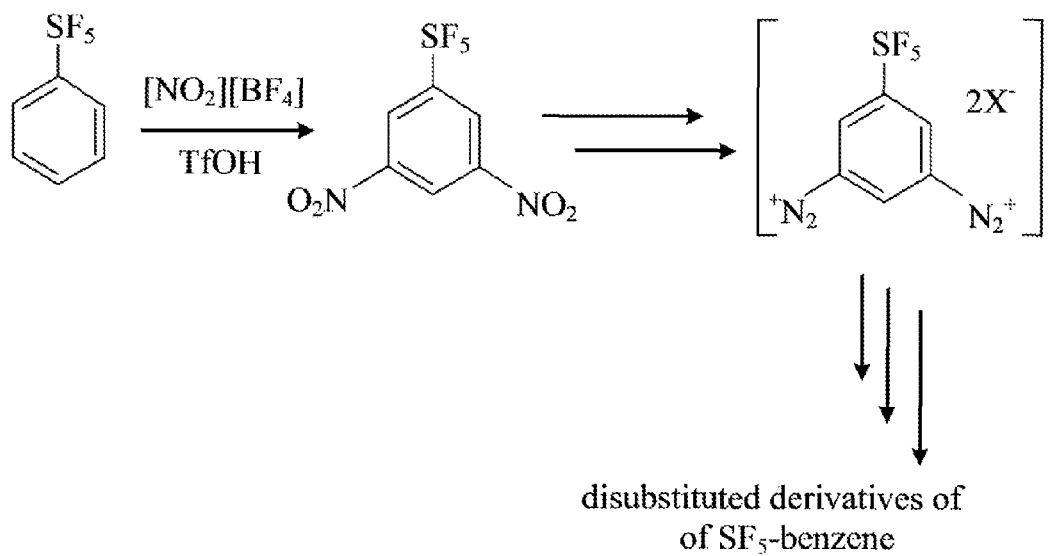
FIG. 6 is a reaction scheme showing bis-diazonium salt synthesis from the dinitro-derivative
Figure 7:
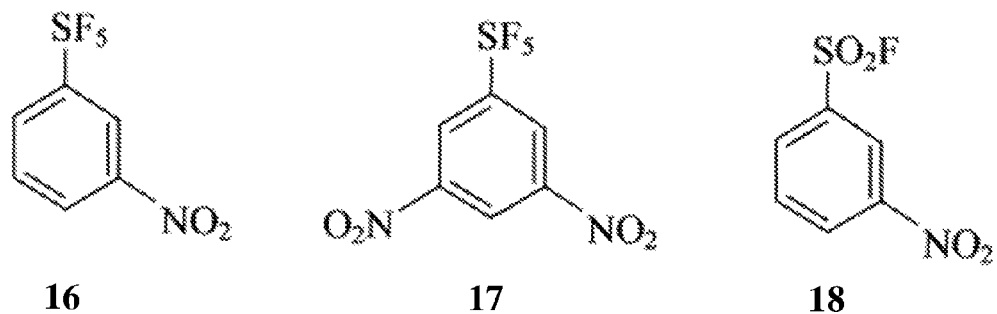
FIG. 7 is an illustration of the products from the nitration of pentafluorosulfonyl compounds.

The dinitro derivative 17 was synthesized from 16 by reaction with NO$_2$+BF$_4$− in TfOH at 70° C. The mono-nitrated pentafluorosulfanyl benzene, in this case 1-nitro-3-(pentafluorosulfanyl)benzene, was heated in neat TfOH to 70° C. with excess nitronium tetrafluoroborate. After 14 days, the desired 1,3-dinitro-5-(pentafluorosulfanyl)benzene 17 was synthesized along with isomers 18 and 19 in a ratio of 85:10:5, as seen in FIG. 6. Its silica gel column chromatographic separation afforded pure 17 in 17% yield, 19 in 2% yield, and 18 in 1% yield, as seen in Table 6 and FIG. 7.

Figure 8:
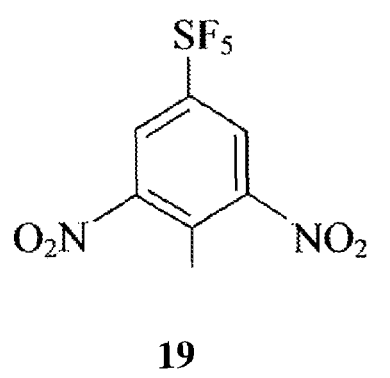
FIG. 8 is an illustration of the products from the nitration of para methyl SF5-Ph.
Figure 8:
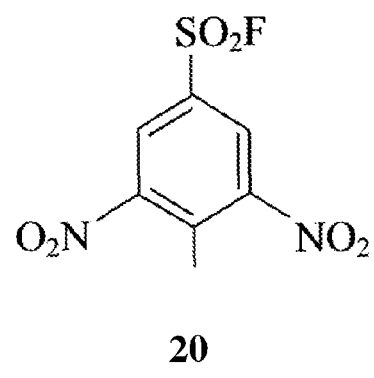
Figure 8:
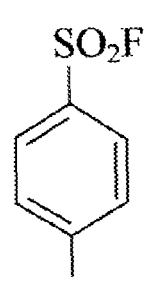

Additionally, alkyl-substituted derivatives can also be synthesized using the same reaction scheme, as seen in Table 7. Reacting p-MeC$_6$H$_4$SF$_5$ with NO$_2$+BF$_4$ in CH$_2$Cl$_2$, followed by heating to 70° C. in TfOH with excess nitronium tetrafluoroborate, formed 2-methyl-1,3-dinitro-5-(pentafluorosulfanyl)benzene 21, along with 5-(fluorosulfonyl)-2-methyl-1,3-dinitrobenzene 22, and 1-(fluorosulfonyl)-4-methyl-benzene 23 in a ratio of 77:19:4, as determined by $^1$H NMR. Silica gel column chromatography purification resulted in pure 21 in 47% isolated yield, and 5-(fluorosulfonyl)-2-methyl-1,3-dinitrobenzene 22 in 18% yield, seen in Table 7 and FIG. 8.

TABLE 7

Nitration of 7 with nitronium tetrafluoroborate.

19 →[NO$_2$BF$_4$] 20

| Solvent | NO$_2$BF$_4$ | Temperature | Time | Product | Isolated yield, %$^a$ |
|---|---|---|---|---|---|
| CH$_2$Cl$_2$ | 1.3 eq | rt | 19 h | 8 | 89 |
| ClCH$_2$CH$_2$Cl | 2.6 eq | 70° C. | 15 h | 8 | 89 |
| TfOH | 2.2 eq | 70° C. | 3 d | 9, 10, 11 | 47% (9); 18% (10); trace (11)$^b$ |

$^a$Isolated yield after SiO$_2$ column chromatography.
$^b$Detected by NMR in the crude reaction mixture.

The dinitro-derivatives, synthesized above, were then converted into a di-amino compound, using known reaction schemes. The dinitro-derivatives are then reduced to amines, followed by diazotization, as discussed in Example 3.

Example 6

Sonogashira coupling was performed with phenylacetylene and its mono- and bis-trifluoromethyl derivatives employing Pd(OAc)$_2$/NaI (Fabrizi, et al., *Angew. Chem.* 2010, 122, 4161-4164) in 95% EtOH/Et$_3$N as solvent at 70° C. The reaction, using the diazonium salt prepared in Example 1, resulted in modest isolated yields of adducts 24a-c, as seen in Table 8. In control experiments no conversion was observed in CH$_3$CN/Et$_3$N/PPh$_3$ at 70° C. Reactions using EtOH alone or EtOH/Na$_2$CO$_3$ at room temp. in the absence of NaI also failed to afford the desired coupling products.

TABLE 8

Sonogashira coupling with phenylacetylenes.

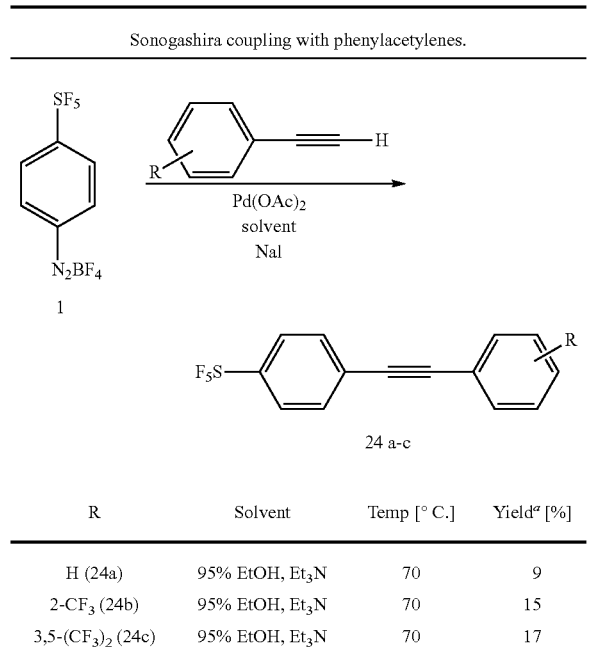

| R | Solvent | Temp [° C.] | Yield$^a$ [%] |
|---|---|---|---|
| H (24a) | 95% EtOH, Et$_3$N | 70 | 9 |
| 2-CF$_3$ (24b) | 95% EtOH, Et$_3$N | 70 | 15 |
| 3,5-(CF$_3$)$_2$ (24c) | 95% EtOH, Et$_3$N | 70 | 17 |

$^a$Isolated yield after SiO$_2$ column chromatography.

Example 7

Dediazoniation of the diazonium salt was undertaken using halo-dediazoniation, azido-dediazoniation, cyano-dediazoniation and thiocyanation of the salt in IL solvent. Reaction of SF$_5$-diazonium salt 1 with TMSX (X=N$_3$, I) and with NH$_4$SCN in 1-butyl-3-methylimidazolium tetrafluoroborate [BMIM][BF$_4$] solvent provided convenient access to compound library 25 through a dediazoniation route (Laali, et al., *J. Org. Chem.* 2007, 72, 6758-6762). Reaction with TMSBr, TMSCl, and TMSCN/KF, on the other hand, generated only traces of targeted SF$_5$ compounds, as seen in Table 9. Fortunately, the X-ray structure of thiocyanate derivative 25c was successfully obtained, confirming structure assignments (data not shown).

TABLE 9

Reaction of 1 with TMSX (X = N3, I, Br, Cl, CN) and with NH$_4$SCN in [BMIM][BF$_4$].

| Reagent | Temp [° C.] | Time [h] | Product | Yield$^a$ [%] |
|---|---|---|---|---|
| TMSN$_3$ (25a) | r.t | 0.1 | | 86 |
| TMSI (25b) | r.t. | 0.1 | | 40 |
| NH$_4$SCN (25c) | 70 | 0.5 | | 31 |
| TMSCl (25d) | r.t. | 48 | | trace$^b$ |
| TMSBr (25e) | r.t. | 62 | | 9 |
| TMSCN/KF (25f) | r.t. | 48 | | trace$^b$ |

$^a$Isolated yield after SiO$_2$ column chromatography.
$^b$Detected by GC-MS.

Example 8

Azide derivative 25a was found to take part in click chemistry with phenylacetylene and its CF$_3$-substituted derivatives when using Cu—Zn nanopowder as catalyst, (Aridoss & Laali, *Eur. J. Org. Chem.* 2011, 6343-6355) to give the corresponding triazole derivatives in isolated yields ranging from 52-63%, as seen in Table 10.

TABLE 10

Synthesis of triazole derivatives 26 by click chemistry.

| R | Temp [° C.] | Time [h] | Yield$^a$ [%] |
|---|---|---|---|
| H (26a) | 70 | 19 | 52 |
| 2-CF$_3$ (17b) | 70 | 19 | 65 |
| 2,5-(CF$_3$)$_2$ (17c) | 70 | 19 | 63 |

$^a$Isolated yield after SiO$_2$ column chromatography.

Example 9

The $SF_5$-diazonium salt took part in azo-coupling reactions with dimethoxy- and isomeric trimethoxybenzenes in EtOH solvent, simply by mixing at room temp. to give corresponding diazo derivatives 27 in 72-98% isolated yields, as seen in Table 11. Coupling reactions with less reactive arenes (phenol and aniline) were much slower and required prolonged reaction times. Attempted diazo-coupling with anisole, 1-methylnaphthalene, 9-methylanthracene, anthracene, 2,6-lutidine, and benzyl cyanide under a variety of conditions were unsuccessful.

TABLE 11

Synthesis of diazo derivatives 27 by azo-coupling.

| R | Solvent | Temp [° C.] | Time | Yield[a] [%] |
|---|---|---|---|---|
| 2,4-(MeO)$_2$ (27a) | 95% EtOH | r.t. | 2 weeks | 98 |
| 2,4,6-(MeO)$_3$ (27b) | 95% EtOH | r.t. | 6 min | 75 |
| 2,4,5-(MeO)$_3$ (27c) | 95% EtOH | r.t. | 6 min | 72 |
| 4-HO (27d) | CH$_3$CN | 70 | 16 h | 0[b] |
| 4-HO (27e) | CH$_3$CN + AcONa | r.t. | 1 month | 62 |
| 4-NH$_2$ (27f) | 95% EtOH | r.t. | 20 days | 22 |

[a]Isolated yield after SiO$_2$ column chromatography.
[b]NMR monitoring.

Example 10

Homoytic dediazoniation can, in principle, serve as an alternative route to Suzuki coupling for the synthesis of unsymmetrical biaryls. Dediazoniation of 1 in MeCN/NaI (Kosynkin, et al., *J. Chem. Soc. Perkin Trans.* 2 1997, 2003-2012) at room temperature in the presence of reactive arenes (mesitylene, p-xylene, and anisole) led to formation of desired unsymmetrical $SF_5$-biaryls 28 in modest yields, as seen in Table 12. Notably, formation of iodo derivatives 25b was a competing reaction.

TABLE 12

Synthesis of biaryl derivatives by homolytic dediazoniation.

| Reagent | Yield of 19[a] [%] |
|---|---|
| 2,4,6-Me$_3$ (28a) | 31 (25b; 60%) |
| 2,5-Me$_2$ (28b) | 14 (25b; 14%) |
| 2,3,5,6-Me$_4$ (28c) | 2 |
| 2,3,4,5,6-Me$_5$ (28d) | trace[b] |
| MeO (28e) | ortho (13), meta (4), para (5)[c] |
| Et (28f) | 0 |

[a]Isolated yield after SiO$_2$ column chromatography.
[b]Detected by GC-MS.
[c]As determined by NMR spectroscopy.

Example 11

Solvolytic dediazoniation of 1 was studied in MeOH, TFE, TfOH, TFAH, HFIP, and in [BMIM][X] ionic liquids with X=PF$_6$, BF$_4$, and NTf$_2$ as counterions, and the progress of each reaction was monitored by $^1$H and $^{19}$F NMR spectroscopy.

Solvolysis in MeOH

Figure 9:
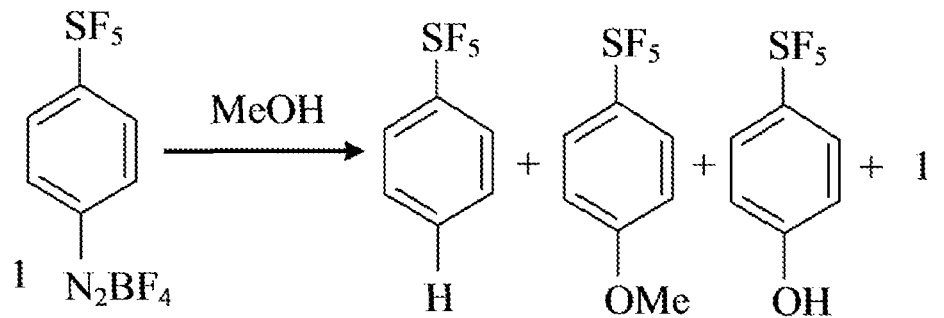
FIG. 9 is a reaction scheme showing dediazoniation of diazonium salts in MeOH.

Diazonium salt 1 reacted slowly in MeOH at room temperature to give Ph-SF$_5$ as a major product along with p-SF$_5$—C$_6$H$_4$OH and p-SF$_5$—C$_6$H$_4$OMe as minor products. The rate of dediazoniation was found to increase in warm MeOH; the reaction was nearly complete after 90 min. The observed product distribution, seen in FIG. 9, is consistent with homolytic dediazoniation as the predominant mechanistic pathway (Zollinger, in: *Diazo Chemistry I*, VCH Verlagsgesellschaft, Weinheim, Germany, 1994, chapter 8).

Solvolysis in TFE

Figure 10:
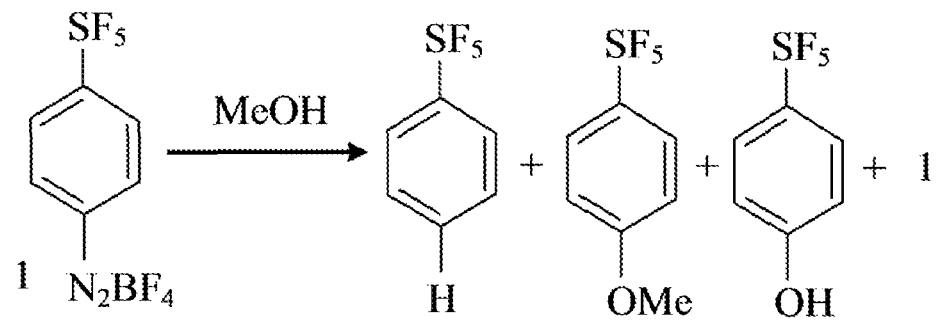
FIG. 10 is a reaction scheme showing dediazoniation of diazonium salts in TFE and TfOH.

Solvolysis of diazonium salt 1 in TFE was very slow at room temperature; even after a reaction time of 7 d 94% of 1 remained unreacted. The rate of reaction could be improved by heating at 70° C., seen in FIG. 10, for four hours. Formation of p-SF$_5$—C$_6$H$_4$—OCH$_2$CF$_3$ 29 and p-SF$_5$—C$_6$H$_4$—F 21 is consistent with heterolytic dediazoniation (Canning, et al., *Chem. Commun.* 1998, 1971-1972). Compound 29, the major product in the mixture, was obtained in 29% isolated yield.

Solvolysis in TfOH

The diazonium salt remained unreacted in TfOH after 3 d of stirring at room temperature. However, dediazoniation proceeded slowly at 50° C. over the course of 1 month to furnish triflate derivative 31, seen in FIG. 10, with concomitant transformation of the SF$_5$ moiety to SO$_2$F. Under these conditions 31 was found to be generated cleanly (>95% by NMR) and was isolated in quantitative yield. The results are consistent with heterolytic dediazoniation in TFE and in TfOH.

Solvolysis in TFAH

Solvolytic dediazoniation of 1 in TFAH was studied at 70° C. Concomitant transformation of the SF$_5$ moiety to its SO$_2$F congener was again observed. The ester p-SF$_5$—C$_6$H$_4$—

Figure 11:
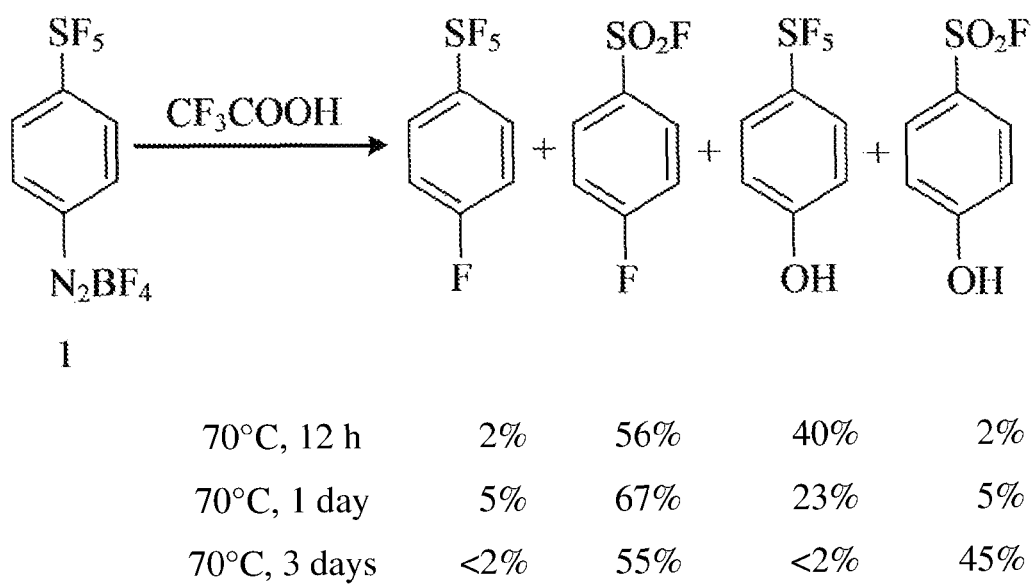
FIG. 11 is a reaction scheme showing dediazoniation of diazonium salts in TFAH.

OCOCF$_3$ was not detected among the products. The evolution of the solvolytic products, as monitored by NMR, as seen in FIG. 11, suggests a heterolytic dediazoniation mechanism and oxidation of the SF$_5$ functionality to SO$_2$F as major events.

Solvolysis in HFIP

Figure 12:
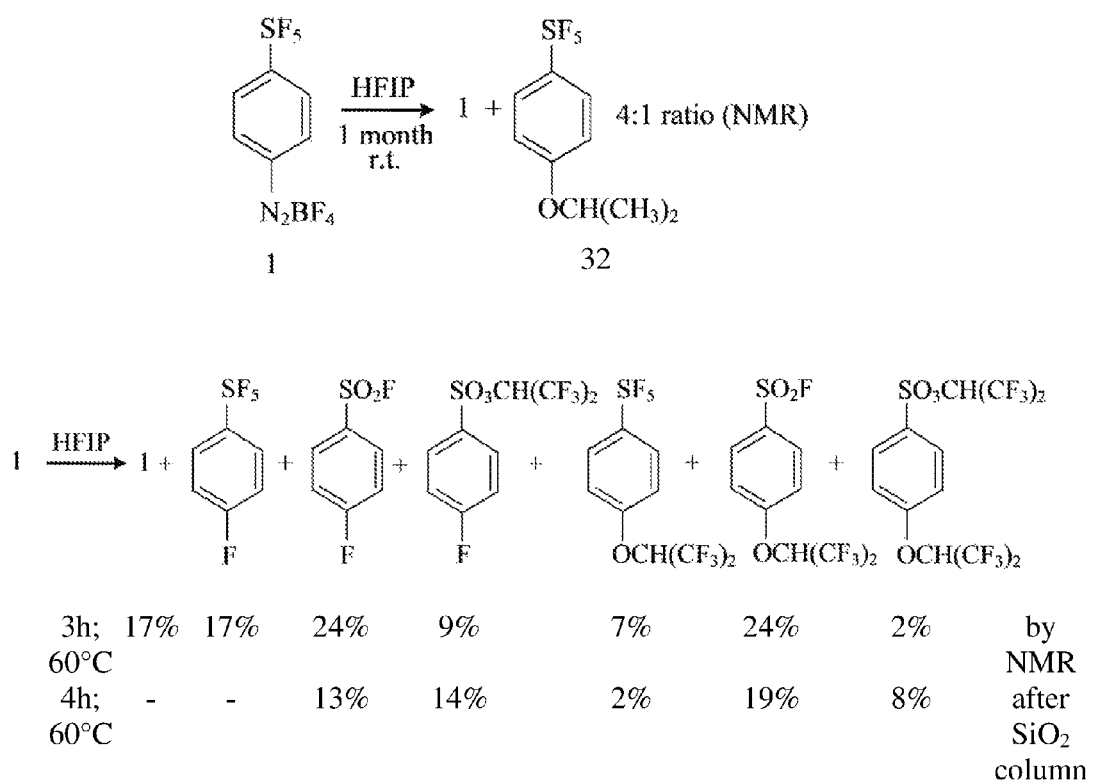
FIG. 12 is a reaction scheme showing dediazoniation of diazonium salts in HFIP.

Solvolysis of 1 in HFIP was very slow at room temperature. After stirring for 1 month p-SF$_5$—C$_6$H$_4$—OCH(CF$_3$)$_2$ 32 was detected by NMR together with unreacted 1. To speed up the process, the reaction was followed at 60° C. where competing oxidation led to a complex mixture which was analyzed by $^1$H and $^{19}$F NMR, as seen in FIG. 12. The solvolytic products observed in HFIP are in accord with a heterolytic mechanism.

Solvolysis in Ionic Liquids

Figure 13:
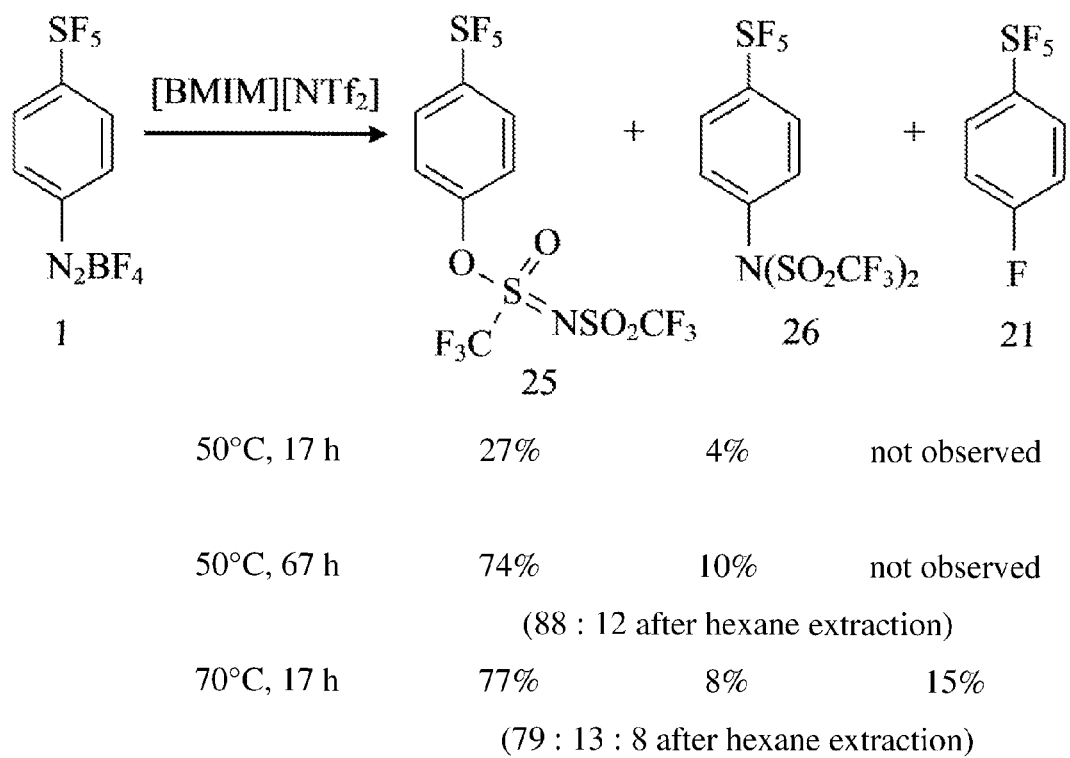
FIG. 13 is a reaction scheme showing dediazoniation of diazonium salts in [BMIM][NTf$_2$].

Solvolytic dediazoniation in 1-butyl-3-methylimidazolium tetrafluoroborate [BMIM][BF$_4$] and [BMIM][PF$_6$] provides easy access to p-SF$_5$—C$_6$H$_4$—F 30 through fluorodediazoniation (Hubbard, et al., *J. Org. Chem.* 2008, 73, 316-319). Reactions were performed at 50° C. and 70° C. and proceeded to completion within a matter of days. In line with related earlier studies (Laali, et al., *J. Org. Chem.* 2007, 72, 6758-6762), solvolytic dediazoniaton of 1 in [BMIM][NTf$_2$] gave 25 as the major and 26 as the minor trapping products consistent with the ambident nucleophilic character of NTf$_2$ anion. Minor amounts of the fluorodediazoniation product p-SF$_5$—C$_6$H$_4$—F 30 were also formed at higher temperatures, as seen in FIG. 13.

Compound 34 was isolated as an oil, and attempts to crystallize it were unsuccessful. By contrast, minor product 35 was isolated as a crystalline solid and its X-ray structure successfully determined thus validating initial structure assignments (data not shown).

Collectively, product analysis of dediazoniation reactions with 1 in highly ionizing low nucleophilicity solvents (TFE, HFIP), protic acids (TfOH, TFAH) and imidazolium ionic liquids underscore the significance of heterolytic dediazoniation and point to the involvement of SF$_5$—C$_6$H$_4^+$ as a critical intermediate. Homolytic dediazoniation was found to be significant only in the MeOH case. To elucidate the relative stability of p-SF5-C$_6$H$_4^+$ the isodesmic reaction was determined by DFT calculations at various levels for both the singlet and triplet phenyl cation species, with R=NO$_2$, CF$_3$, and H.

Solvent effects were also considered using PCM calculations. The computed relative energies imply the relative stability order as Ph$^+$>>p-CF$_3$C$_6$H$_4^+$>p-NO$_2$—C$_6$H$_4^+$≈p-F$_5$S—C$_6$H$_4^+$ for the phenyl cation intermediates. In concert with an earlier DFT study of aryl cations (Laali, et al., *J. Org. Chem.* 2002, 67, 2913-2918), the singlet 4-R-phenyl cations are more stable than the corresponding triplet cations. Whereas a p-NO$_2$ group is more effective in stabilizing the singlet state relative to triplet state, a p-SF$_5$ group stabilizes the singlet and triplet phenyl cations to the same extent.

Example 12

General

NMR spectra were recorded with a 500 MHz spectrometer at room temperature ($^1$H: 500 MHz, $^{19}$F: 470 MHz, 13C: 125 MHz). IR data were collected with an FT-IR instrument. Electron ionization mass spectra (EI-MS) were measured using a GC-MS instruments. All reagents were commercially available and were used without purification.

4-(Pentafluorosulfanyl)benzenediazonium Tetrafluoroborate (1)

A solution of 1-(pentafluorosulfanyl)benzene (495.9 mg, 2.263 mmol) in CH$_2$Cl$_2$ (10 mL) was added dropwise to BF$_3$.OEt$_2$ (493.3 mg, 3.476 mmol) in a flask cooled with an ice-water bath. tert-Butyl nitrite (300.1 mg, 2.910 mmol) in 2 mL of CH$_2$Cl$_2$ was added dropwise and stirred at 0° C. for 1 h. The precipitated colorless crystals were isolated by filtration. The crystals was dissolve in CH$_3$CN (0.4 mL) and precipitated by addition of ether to give pale yellow solid crystals, which were washed with diethyl ether. Removal of the solvent under vacuum afforded the title compound as pale yellow crystals (605.1 mg, 84%): IR (ATR): ṽ=2924, 2852, 2309, 1574, 1418, 1304, 1053, 768 cm$^{-1}$. $^1$H NMR (500 MHz, CD$_3$CN): δ=8.72 (d, J=9.2 Hz, 2H), 8.40 (d, J=9.2 Hz, 2H) ppm. $^{13}$C NMR (125 MHz, CD$_3$COCD$_3$): δ=160.4, (C), 134.4 (2CH), 129.5 (2CH), 120.4 (C) ppm. $^{19}$F NMR (470 MHz, CD$_3$CN): δ=77.7 (quint, J=151 Hz, 1 F), 60.9 (d, J=151 Hz, 4 F), −151.5 (s, 4 F) ppm.

(E)-4-(Pentafluorosulfanyl)stilbene 2a i) EtOH as Solvent: A solution of 1 (10.0 mg, 0.0315 mmol) in 0.4 mL of 95% aqueous ethanol was added dropwise to a solution of styrene (6.5 mg, 0.062 mmol) and palladium(II) acetate (0.5 mg, 0.002 mmol) in 0.11 g of 95% aqueous ethanol. The reaction mixture was heated by an oil bath at 70° C. for 15 h. After cooling, the mixture was filtered through a pad of Celite 545 and purified by SiO$_2$ column chromatography (9:1 hexane/CH$_2$Cl$_2$) to give 2a (7.4 mg, 77% yield) as colorless crystals; m.p. 121.6-122.0° C. IR (ATR): ṽ=3028, 1593, 1499, 1450, 1096, 964 cm$^{-1}$. MS (GC, EI): m/z=306 [M$^+$], 179. $^1$H NMR (500 MHz, CDCl$_3$): δ=7.73 (d, J=8.5 Hz, 2H), 7.56 (d, J=8.5 Hz, 2H), 7.53 (d, J=7.4 Hz, 2H), 7.39 (t, J=7.4 Hz, 2H), 7.31 (t, J=7.4 Hz, 1H), 7.19 (d, J=16.4 Hz, 1H), 7.09 (d, J=16.4 Hz, 1H) ppm. $^{13}$C NMR (125 MHz, CDCl$_3$): δ=152.5 (C), 140.6 (C), 136.4 (C), 132.0 (CH), 128.8 (2CH), 128.5 (CH), 126.8 (2CH), 126.3 (5CH) ppm. $^{19}$F NMR (470 MHz, CDCl3): δ=89.9 (quint, J=150.2 Hz, 1 F), 61.0 (d, J=150.2 Hz, 4 F) ppm.

ii) [BMIM][BF$_4$] as Solvent: Palladium(II) acetate (0.5 mg, 0.002 mmol) was added to a solution of 1 (10.5 mg, 0.0330 mmol) and styrene (29.0 mg, 0.278 mmol) in 96.6 mg of [BMIM][BF$_4$]. The mixture was stirred at room temp. for 22 h and was extracted with diethyl ether (0.5 mL×3). The solvent of the combined organic layer was evaporated to give a brown oil, which was purified by SiO$_2$ column chromatography (9:1 hexane/CH$_2$Cl$_2$) to give 2a (2.3 mg, 23% yield) as colorless crystals.

(E)-4-Fluoro-4'-(pentafluorosulfanyl)stilbene (2b)

A solution of 1 (10.4 mg, 0.0315 mmol) in 0.4 mL of 95% aqueous ethanol was added dropwise to a solution of 4-fluorostyrene (9.8 mg, 0.080 mmol) and palladium(II) acetate (0.2 mg, 0.0009 mmol) in 0.10 g of 95% aqueous ethanol. The reaction mixture was heated on an oil bath at 70° C. for 5 h. After cooling, the mixture was filtered through a pad of Celite 545 and purified by SiO$_2$ column chromatography (9:1 hexane/CH$_2$Cl$_2$) to give 2b (8.2 mg, 77% yield) as colorless crystals; m.p. 85.0-86.2° C. IR (ATR): ṽ=1593, 1508, 1236, 1159, 1099, 964, 831, 818 cm$^{-1}$. MS (GC, EI): m/z=324 [M$^+$], 197 [M$^+$ SF$_5$], 177. $^1$H NMR (500 MHz, CDCl$_3$): δ=7.73 (d, J=8.8 Hz, 2H), 7.55 (d, J=8.5 Hz, 2H), 7.51 (dd, J=8.8, 5.4 Hz, 2H), 7.15 (d, J=16.4 Hz, 1H), 7.08 (d, J=8.7 Hz, 2H), 7.01 (d, J=16.4 Hz, 1H) ppm. $^{13}$C NMR (125 MHz, CDCl$_3$): δ=162.8 (C), 152.3 (C), 140.4 (C), 132.6 (C), 130.7 (CH), 128.4 (2CH), 126.3 (2CH), 126.2 (2CH), 126.2 (CH), 115.8 (2CH) ppm. $^{19}$F NMR (470 MHz, CDCl$_3$): δ=84.9 (quint, J=150.2 Hz, 1 F), 63.0 (d, J=150.2 Hz, 4 F), −112.7 (m, 1 F) ppm.

(E)-4-Methyl-4'_-(pentafluorosulfanyl)stilbene (2c)

A solution of 1 (10.0 mg, 0.0315 mmol) in 0.4 mL of 95% aqueous ethanol was added dropwise to a solution of 4-methylstyrene (9.0 mg, 0.076 mmol) and palladium(II) acetate (0.2 mg, 0.0009 mmol) in 0.12 g of 95% aqueous ethanol. The reaction mixture was heated on an oil bath at 70° C. for 5 h. After cooling, the mixture was filtered through a pad of Celite 545 and purified by SiO$_2$ column chromatography (9:1 hexane/CH$_2$Cl$_2$) to give 2c (8.3 mg, 82% yield) as colorless crystals; m.p. 165.2-166.5° C. IR (ATR): ṽ=1593, 1514, 1450, 1416, 1329, 1265, 1098, 972, 962, 841 cm$^{-1}$. MS (GC, EI): m/z=320 [M$^+$], 193 [M$^+$-F$_5$S], 178 [M$^+$-CH$_3$F$_5$S]. $^1$H NMR (500 MHz, CDCl$_3$): δ=7.72 (d, J=8.8 Hz, 2H), 7.54 (d, J=8.5 Hz, 2H), 7.43 (d, J=8.1 Hz, 2H), 7.19 (d, J=8.0 Hz, 2H), 7.16 (d, J=16.4 Hz, 1H), 7.04 (d, J=16.4 Hz, 1H), 2.38 (s, 3H) ppm. $^{13}$C NMR (125 MHz, CDCl$_3$): δ=152.3 (C), 140.8 (C), 138.6 (C), 133.6 (C), 131.9 (CH), 129.5 (2CH), 126.7 (2CH), 126.3 (2CH), 126.2 (2CH), 125.3 (CH), 21.3 (CH3) ppm. $^{19}$F NMR (470 MHz, CDCl$_3$): δ=85.1 (quint, J=150 Hz, 1 F), 63.1 (d, J=150 Hz, 4 F) ppm.

(E)-4-Chloro-4_-(pentafluorosulfanyl)stilbene (2d)

Palladium(II) acetate (0.5 mg, 0.002 mmol) was added to a solution of 1 (10.76 mg, 0.0337 mmol) and 4-chlorostyrene (19.0 mg, 0.137 mmol) in 0.18 g of 95% aqueous ethanol. The reaction mixture was stirred at room temperature for 1 d. The mixture was filtered through a pad of Celite 545 with CH$_2$Cl$_2$ and purified by SiO$_2$ column chromatography with hexane as eluent to give 2d (7.5 mg, 65% yield) as colorless crystals; m.p. 119.8-120.8° C. MS (GC, EI): m/z=340 [M$^+$], 321, 232, 213, 196, 178 [M$^+$ ClF$_5$S]. IR (ATR): ṽ=1589, 1495, 1414, 1094, 970, 831 cm$^{-1}$. $^1$H NMR (500 MHz, CDCl$_3$): δ=7.73 (d, J=8.7 Hz, 2H), 7.55 (d, J=8.7 Hz, 2H), 7.46 (d, J=8.5 Hz, 2H), 7.35 (d, J=8.5 Hz, 2H), 7.13 (d, J=16.4 Hz, 1H), 7.06 (d, J=16.4 Hz, 1H) ppm. $^{13}$C NMR (125 MHz, CDCl$_3$): δ=152.7 (C), 140.2 (C), 134.9 (C), 134.1 (C), 130.6 (CH), 129.0 (2CH), 128.0 (2CH), 126.9 (CH), 126.4 (4CH) ppm. $^{19}$F NMR (470 MHz, CDCl$_3$): δ=84.8 (quint, J=150 Hz, 1 F), 63.0 (d, J=150 Hz, 4 F) ppm.

(E)-4-Acetoxy-4_-(pentafluorosulfanyl)stilbene (2e)

Palladium(II) acetate (0.5 mg, 0.002 mmol) was added to a solution of 1 (11.6 mg, 0.0365 mmol) and 4-acetoxystyrene (11.5 mg, 0.0709 mmol) in 0.22 g of 95% aqueous ethanol. The reaction mixture was stirred at room temperature for 14 h, filtered through a pad of Celite 545 with CH$_2$Cl$_2$, and purified by SiO$_2$ column chromatography (1:1 hexane/CH$_2$Cl$_2$) to give 2e (8.5 mg, 64% yield) as colorless crystals; m.p. 177.5-178.5° C. MS (GC, EI): m/z=364 [M$^+$], 322 [M$^+$-COCH$_2$], 194, 165. IR (ATR): ṽ=1759, 1593, 1508, 1373, 1223, 833 cm$^{-1}$. $^1$H NMR (500 MHz, CDCl$_3$): δ=7.73 (d, J=8.7 Hz, 2H), 7.55 (d, J=8.4 Hz, 2H), 7.54 (d, J=8.7 Hz, 2H), 7.16 (d, J=16.4 Hz, 2H), 7.12 (d, J=8.4 Hz, 2H), 7.04 (d, J=16.4 Hz, 1H), 2.32 (s, 3H) ppm. $^{13}$C NMR (125 MHz, CDCl$_3$): δ=169.4 (C), 152.6 (C), 150.7 (C), 140.4 (C), 134.2 (C), 130.9 (CH), 127.8 (2CH), 126.6 (CH), 126.3 (4CH), 122.0 (2CH), 21.1 (CH$_3$) ppm. $^{19}$F NMR (470 MHz, CDCl$_3$): δ=84.9 (quint, J=150 Hz, 1 F), 63.1 (d, J=150 Hz, 4 F) ppm.

Methyl (E)-3-[4-(Pentafluorosulfanyl)phenyl]prop-2-enoate (3)

(Bowden, et al., *Tetrahedron* 2000, 56, 3393-3408) Palladium(II) acetate (0.5 mg, 0.002 mmol) was added to a solution of 1 (10.9 mg, 0.0343 mmol) and methyl acrylate (15.6 mg, 0.181 mmol) in 0.18 g of 95% aqueous ethanol. The reaction mixture as stirred at room temperature for 18 h, filtered through a pad of Celite 545 with CH$_2$Cl$_2$, and purified by SiO$_2$ column chromatography (6:4 hexane/CH$_2$Cl$_2$) to give 3 (8.4 mg, 85% yield) as colorless crystals; m.p. 80.5-81.5° C. MS (GC, EI): m/z=288 [M$^+$], 269 [M$^+$-F], 257, 130, 102. IR (ATR): ṽ=1701, 1640, 1439, 1317, 1213, 1101, 999, 845, 816 cm$^{-1}$. $^1$H NMR (500 MHz, CDCl$_3$): δ=7.78 (d, J=8.7 Hz, 2H), 7.68 (d, J=16.1 Hz, 1H), 7.60 (d, J=8.7 Hz, 2H), 7.61 (d, J=16.1 Hz, 1H), 3.83 (s, 3H) ppm. $^{13}$C NMR (125 MHz, CDCl$_3$): δ=166.7 (C), 154.6 (C), 142.5 (CH), 137.5 (C), 128.0 (2CH), 126.6 (2CH), 121.1 (CH), 52.0 (CH3) ppm. $^{19}$F NMR (470 MHz, CDCl$_3$): δ=83.7 (quint, J=150 Hz, 1 F), 62.6 (d, J=150 Hz, 4 F) ppm.

Methyl (E)-2-Methyl-3-(pentafluorosulfanyl)prop-2-enoate 4 and Methyl 2-{[4-(Pentafluorosulfanyl)phenyl]methyl}prop-2-enoate (5)

i) In EtOH. Method a: A solution of 1 (10.2 mg, 0.0321 mmol) in 0.4 mL of 95% aqueous ethanol was added dropwise to a solution of methyl methacrylate (8.9 mg, 0.089 mmol) and palladium(II) acetate (0.2 mg, 0.0009 mmol) in 0.12 g of 95% aqueous ethanol. The reaction mixture was heated on an oil bath at 70° C. for 4 h. After cooling, the mixture was filtered through a pad of Celite 545. Removal of the solvent gave a brown oil, whose NMR analysis showed the formation of 4 and 5 in 1:2 ratio (17.8 mg). The products were purified by SiO$_2$ column chromatography (6:4 hexane/CH$_2$Cl$_2$). The first eluted product was 5 (colorless oil; 1.2 mg, 12%). The second fraction was a mixture of 5 and 4 (pale yellow oil; 1:1 ratio, 2.8 mg, 29%), and the next fraction was pure 4 (pale yellow oil; 0.6 mg, 6%).

Method b: To a solution of 1 (20.8 mg, 0.0654 mmol) and methyl methacrylate (19.0 mg, 0.190 mmol) in 0.76 g mL of 95% aqueous ethanol was added palladium(II) acetate (0.5 mg, 0.002 mmol). The reaction mixture was heated on an oil bath at 70° C. for 2 h. After cooling, the mixture was filtered through a pad of Celite 545 to give a pale brown oil, whose NMR analysis showed the formation of 4 and 5 in 1:2 ratio (32.7 mg). The products were purified by SiO$_2$ column chromatography (7:3 hexane/CH$_2$Cl$_2$) to give a mixture of both compounds (15.5 mg) as colorless oil (78%). Subsequent preparative TLC (1:1 hexane/CH$_2$Cl$_2$) separation of the mixture gave: The first eluted product was 5 (colorless oil; 9.6 mg, 48%). The second fraction was a mixture of the two compounds (pale yellow oil; 1:1 ratio, 11.1 mg, 56%) and the next fraction was pure 4 (pale yellow oil; 1.8 mg, 9%).

ii) in [BMIM][BF$_4$]: To a solution of 1 (11.3 mg, 0.0355 mmol) and methyl methacrylate (20.0 mg, 0.200 mmol) in 0.11 g of [BMIM][BF$_4$] was added palladium(II) acetate (0.5 mg, 0.002 mmol). The reaction mixture was stirred at room temp. for 16 h. NMR analysis of the reaction mixture showed the formation of 4 and 5 in 1:3 ratio and complete consumption of the diazonium ion. The reaction mixture was extracted with diethyl ether and the solvent was evaporated to give a pale-brown oil. The products were purified by SiO$_2$ column chromatography (8:2 hexane/CH$_2$Cl$_2$) to give a mixture of the two compounds (10.6 mg) as colorless oil (99%).

Methyl 2-Methylidene-3-(pentafluorosulfanyl)propanoate (4)

IR (ATR): ṽ=2916, 2849, 1717, 1439, 1261, 1117, 847 cm$^{-1}$. MS (GC, EI): m/z=302 [M$^+$], 242 [M$^+$-C$_2$H$_4$O$_2$], 115 [M$^+$-C$_2$H$_4$F$_5$O$_2$S]. $^1$H NMR (500 MHz, CDCl$_3$): δ=7.67 (d, J=8.5 Hz, 2H), 7.30 (d, J=8.5 Hz, 2H), 6.29 (s, 1H), 5.56 (s, 1H), 3.74 (s, 3H), 3.68 (s, 2H) ppm. $^{19}$F NMR (470 MHz, CDCl$_3$): δ=85.3 (quint, J=150.2 Hz, 1 F), 63.2 (d, J=150.2 Hz, 4 F) ppm. $^{13}$C NMR (125 MHz, CDCl$_3$): δ=168.5 (C), 153.1 (C), 139.2 (C), 136.5 (CH), 131.1 (C), 129.6 (2CH), 126.0 (2CH) ppm.

Methyl 2-{[4-(Pentafluorosulfanyl)phenyl]methyl}prop-2-enoate (5)

IR (ATR): ṽ=2955, 1721, 1632, 1441, 1207, 1142, 1099, 840 cm$^{-1}$. MS (GC, EI): m/z=302 [M$^+$], 116 [M$^+$-C$_2$H$_3$F$_5$O$_2$S], 115 [M$^+$-C$_2$H$_4$F$_5$O$_2$S]. $^1$H NMR (500 MHz, CDCl$_3$): δ=7.77 (d, J=8.5 Hz, 2H), 7.66 (s, 1H), 7.45 (d, J=8.5 Hz, 2H), 3.84 (s, CH$_3$), 2.11 (s, CH$_3$) ppm. $^{13}$C NMR (125 MHz, CDCl$_3$): δ=166.9 (C), 152.3 (C), 142.8 (C), 138.9 (C), 129.1 (2CH), 127.2 (CH$_2$), 126.0 (2CH) ppm. $^{19}$F NMR (470 MHz, CDCl$_3$): δ=84.1 (quint, J=150.2 Hz, 1 F), 62.8 (d, J=150.2 Hz, 4 F) ppm.

(E)-3,3,4,4,5,5,6,6,6-Nonafluoro-1-[4-(pentafluorosulfanyl)phenyl]-hex-1-ene (7a)

Palladium(II) acetate (0.5 mg, 0.002 mmol) was added to a solution of 1 (15.0 mg, 0.0472 mmol) and 3,3,4,4,5,5,6,6,6-nonafluorohex-1-ene (8.9 mg, 0.089 mmol) in 0.44 g of 95% aqueous ethanol. The reaction mixture was stirred at room temperature for 1 d and filtered through a pad of Celite 545. Removal of the solvent gave a pale yellow oil which was purified by SiO$_2$ column chromatography with hexane to give 7a as colorless oil (17.1 mg; 81%): IR (ATR): ṽ=2918, 2849, 1663, 1234, 1134, 844 cm$^{-1}$. MS (GC, EI): m/z=448 [M$^+$], 429 [M$^+$-F], 302 [M$^+$-SF$_6$], 279 [M$^+$-C$_3$F$_7$], 152 [M$^+$-C3F12S]. $^1$H NMR (500 MHz, CDCl$_3$): δ=7.80 (d, J=8.7 Hz, 2H), 7.57 (d, J=8.7 Hz, 2H), 7.20 (d, J=16.2 Hz, 1H), 6.30 (dt, J=16.2, 12.0 Hz, 1H) ppm. $^{13}$C NMR (125 MHz, CDCl$_3$): δ=154.7 (C), 137.7 (CH), 136.5 (C), 127.8 (2CH), 126.7 (2CH), 117.7 (CH) ppm. $^{19}$F NMR (470 MHz, CDCl$_3$): δ=83.4 (quint, J=150 Hz, 1 F), 62.6 (d, J=150 Hz, 4 F), −81.0 (s, 3 F), −112.0 (s, 2 F), −124.0 (s, 2 F), −125.7 (s, 2 F) ppm.

(E)-3,3,4,4,5,5,6,6,7,7,8,8,8-Tridecafluoro-1-[4'-(pentafluorothio)-phenyl]oct-1-ene (7b)

Palladium(II) acetate (1.0 mg, 0.0045 mmol) was added to a solution of 1 (22.4 mg, 0.0704 mmol) and 3,3,4,4,5,5,6,6,7,7,8,8,8-undecacfluorooct-1-ene (35.4 mg, 0.102 mmol) in 0.45 g of 95% aqueous ethanol. The reaction mixture was stirred at room temperature for 16 h, and filtered through a pad of Celite 545 with a help of hexane. Removal of the solvent gave a pale brown oil, which was purified by SiO$_2$ column chromatography with hexane to give 7b as colorless oil (31.9 mg; 83%): IR (ATR): ṽ=1238, 1190, 1144, 844 cm$^{-1}$. MS (GC, EI): m/z=548 [M$^+$], 529 [M$^+$-F], 421 [M$^+$-SF$_5$], 402 [M$^+$-SF$_6$], 279 [M$^+$-C$_5$F$_{11}$], 152 [M$^+$-C$_5$F$_{16}$S]. $^1$H NMR (500 MHz, CDCl$_3$): δ=7.80 (d, J=8.6 Hz, 2H), 7.57 (d, J=8.6 Hz, 2H), 7.20 (d, J=16.2 Hz, 1H), 6.30 (dt, J=16.2, 11.8 Hz, 1H) ppm. $^{13}$C NMR (125 MHz, CDCl$_3$): δ=154.7 (C), 137.6 (CH), 136.6 (C), 127.8 (2CH), 126.7 (2CH), 117.8 (CH) ppm. $^{19}$F NMR (470 MHz, CDCl$_3$): δ=83.4 (quint, J=150 Hz, 1 F), 62.6 (d, J=150 Hz, 4 F), −80.8 (s, 3 F), −111.8 (s, 2 F), −121.6 (s, 2 F), −122.9 (s, 2 F), −123.2 (s, 2 F), −126.2 (s, 2 F) ppm.

Camphene Adduct 9:

Palladium(II) acetate (0.3 mg, 0.001 mmol) was added to a solution of 1 (12.9 mg, 0.0406 mmol) and camphene (7.7 mg, 0.057 mmol) in 0.27 g of 95% aqueous ethanol. The reaction mixture was stirred at room temperature for 16 h, and filtered through a pad of Celite 545 with the help of hexane. Removal of the solvent gave a colorless oil, which was purified by SiO$_2$ column chromatography using hexane to give the adduct 9 as colorless oil (12.2 mg; 89%): IR (ATR): ṽ=2965, 1655, 1597, 1495, 1460, 1383, 1101, 841 cm$^{-1}$. MS (GC, EI): m/z=338 [M$^+$], 323 [M$^+$-CH$_3$], 309 [M$^+$-C$_2$H$_5$]. $^1$H NMR (500 MHz, CDCl$_3$): δ=7.67 (d, J=8.8 Hz, 2H), 7.30 (d, J=8.8 Hz, 2H), 6.00 (s, 1H), 3.21 (d, J=4.7 Hz, 1H), 1.99 (d, J=2.2 Hz, 1H), 1.84 (m, 1H), 1.76 (m, 1H), 1.72 (m, 1H), 1.51 (m, 1H), 1.41 (m, 1H), 1.30 (d, J=10.0 Hz, 1H), 1.13 (s, 6H) ppm. $^{13}$C NMR (125 MHz, CDCl$_3$): δ=163 (C), 151.0 (C), 142.5 (C), 127.8 (2CH), 125.7 (2CH), 114.7 (CH), 47.4 (CH), 43.6 (C), 42.6 (CH), 38.0 (CH2), 28.9 (CH$_3$), 27.7 (CH$_2$), 26.1 (CH$_3$), 23.7 (CH$_2$) ppm. $^{19}$F NMR (470 MHz, CDCl$_3$): δ=85.6 (quint, J=150 Hz, 1 F), 63.2 (d, J=150 Hz, 4 F) ppm.

Reaction with Stilbene:

Palladium(II) acetate (0.5 mg, 0.002 mmol) was added to a solution of 1 (11.1 mg, 0.0349 mmol) and stilbene (8.0 mg, 0.044 mmol) in 0.21 g of 95% aqueous ethanol. The reaction mixture was heated an oil bath at 70° C. for 40 min, and filtered through a pad of Celite 545 with the help of hexane. Removal of the solvent gave a colorless crystalline solid, which was purified by SiO$_2$ column chromatography using hexane/CH$_2$Cl$_2$ (8:2) to give a mixture of stilbene, and (Z)-, and (E)-1,2-diphenyl-1-(pentafluorosulfanyl)phenylethenes (11 and 12) (5:2:3 ratio) as colorless crystals (10.1 mg; yield of the adducts, 11 and 12, 45%). 11: $^1$H NMR (500 MHz, CDCl$_3$): δ=7.69 (d, J=8.5 Hz, 2H), 7.40-7.26 (m, 6H), 7.19-7.14 (m, 4H), 7.05-7.02 (m, 2H), 7.04 (s, 1H) ppm. $^{19}$F NMR (470 MHz, CDCl$_3$): δ=84.7 (quint, J=150 Hz, 1 F), 63.0 (d, J=150 Hz, 4 F) ppm. $^{13}$C NMR (125 MHz, CDCl$_3$): δ=144.2 (C), 142.5 (C), 140.6 (C), 136.6 (C), 130.9 (2CH), 129.8 (CH), 129.5 (2CH), 128.4 (2CH), 128.2 (2CH), 128.0 (CH), 127.6 (2CH), 127.3 (CH), 126.2 (2CH) ppm.

12: $^1$H NMR (500 MHz, CDCl$_3$): δ=7.68 (d, J=8.5 Hz, 2H), 7.40-7.26 (m, 6H), 7.19-7.14 (m, 4H), 7.05-7.02 (m, 2H), 7.01 (s, 1H) ppm. $^{19}$F NMR (470 MHz, CDCl$_3$): δ=84.9 (quint, J=150 Hz, 1 F), 63.1 (d, J=150 Hz, 4 F) ppm. $^{13}$C NMR (125 MHz, CDCl3): δ=146.7 (C), 140.6 (C), 139.3 (C), 136.6 (C), 130.5 (CH), 130.2 (2CH), 129.7 (CH), 128.9 (2CH), 128.1 (2CH), 127.9 (CH), 127.6 (2CH), 127.4 (CH), 125.8 (2CH) ppm.

4-(Pentafluorosulfanyl)-4-(trifluoromethyl)biphenyl (13a)

Palladium(II) acetate (0.5 mg, 0.002 mmol) was added to a mixture of 1 (10.8 mg, 0.0340 mmol), 4-(trifluoromethyl)phenylboronic acid (7.3 mg, 0.038 mmol), and Na$_2$CO$_3$ (5.9 mg, 0.056 mmol) in 0.20 g of 95% aqueous ethanol. The reaction mixture was stirred at 70° C. for 3 h, and filtered through a pad of SiO$_2$ with the help of hexane. Removal of the solvent gave a brown crystalline solid, which was purified by SiO$_2$ column chromatography with hexane to give the title compound 13a as colorless crystals (3.2 mg; 27%): m.p. 123.5-125.0° C. IR (ATR): ṽ=2924, 1618, 1492, 1395, 1327, 1171, 1107, 1072, 837, 814 cm$^{-1}$. MS (GC, EI): m/z=348 [M$^+$], 329 [M$^+$-F], 239. $^1$H NMR (500 MHz, CDCl$_3$): δ=7.87

(d, J=8.8 Hz, 2H), 7.75 (d, J=8.8 Hz, 2H), 7.69 (d, J=8.8 Hz, 2H), 7.67 (d, J=8.8 Hz, 2H) ppm. $^{13}$C NMR (125 MHz, CDCl$_3$): δ=153.5 (C), 143.0 (C), 142.5 (C), 130.5 (q, J=33 Hz), 127.7 (2CH), 127.5 (2CH), 126.6 (2CH), 126.0 (2CH), 124.0 (q, J=272 Hz, C) ppm. $^{19}$F NMR (470 MHz, CDCl$_3$): δ=84.2 (quint, J=150 Hz, 1 F), 63.0 (d, J=150 Hz, 4 F), −62.6 (s, 3 F) ppm.

3,4,5-Trifluoro-4-(pentafluorosulfanyl)biphenyl (13b)

Palladium(II) acetate (0.5 mg, 0.002 mmol) was added to a mixture of 1 (14.7 mg, 0.0462 mmol), 3,4,5-trifluorophenylboronic acid (7.1 mg, 0.040 mmol), and Na$_2$CO$_3$ (15.1 mg, 0.14 mmol) in 0.69 g of 95% aqueous ethanol. The reaction mixture was stirred at room temp. for 1 d, and filtered through a pad of SiO$_2$ with the help of hexane. Removal of the solvent gave a brown crystalline solid which was purified by SiO$_2$ column chromatography with hexane to give 13b as a colorless oil (6.0 mg; 44%), which subsequently gave colorless crystals (from hexane); m.p. 46.5-48.8° C. IR (ATR): $\tilde{v}$=1618, 1579, 1537, 1506, 1496, 1449, 1396, 1363, 1254, 1105, 1051, 828 cm$^{-1}$. MS (GC, EI): m/z=334 [M$^+$], 315 [M$^+$-F], 226, 206. $^1$H NMR (500 MHz, CDCl$_3$): δ=7.85 (d, J=8.5 Hz, 2H), 7.58 (d, J=8.5 Hz, 2H), 7.20 (t, J=7.0 Hz, 2H) ppm. $^{13}$C NMR (125 MHz, CDCl$_3$): δ=153.5 (C), 151.5 (d, J=251 Hz, C), 141.4 (C), 140.0 (d, J=254 Hz, C), 135.0 (C), 127.1 (2CH), 126.8 (2CH), 111.5 (d, J=17 Hz, 2CH) ppm. 19F NMR (470 MHz, CDCl$_3$): δ=83.9 (quint, J=150 Hz, 1 F), 63.0 (d, J=150 Hz, 4 F), −132.9 (d, J=8 Hz, 2 F), −160.3 (t, J=8 Hz, 1 F) ppm.

3,5-Dimethyl-4-(pentafluorosulfanyl)biphenyl (13c)

Palladium(II) acetate (0.5 mg, 0.002 mmol) was added to a mixture of 1 (12.2 mg, 0.0384 mmol), 3,5-dimethylphenylboronic acid (5.2 mg, 0.035 mmol), and Na$_2$CO$_3$ (6.7 mg, 0.063 mmol) in 0.48 g of 95% aqueous ethanol. The reaction mixture was stirred at room temp. for 20 h and filtered through a pad of SiO$_2$ with the help of hexane. Removal of the solvent gave a brown crystalline solid which was purified by SiO$_2$ column chromatography with hexane to give 13c (6.3 mg) as a colorless oil (59%): IR (ATR): $\tilde{v}$=3024, 2920, 2853, 1599, 1468, 1379, 1105, 822 cm$^{-1}$. MS (GC, EI): m/z=308 [M$^+$], 293 [M$^+$-CH$_3$], 289 [M$^+$-F], 199, 203, 164. $^1$H NMR (500 MHz, CDCl$_3$): δ=7.79 (d, J=8.5 Hz, 2H), 7.63 (d, J=8.5 Hz, 2H), 7.19 (s, 2H), 7.06 (s, 1H), 2.39 (s, 6H) ppm. $^{13}$C NMR (125 MHz, CDCl$_3$): δ=152.8 (C), 144.8 (C), 139.1 (C), 138.6 (2 C), 130.0 (CH), 127.2 (2CH), 126.2 (2CH), 125.2 (2CH), 21.4 (2CH3) ppm. $^{19}$F NMR (470 MHz, CDCl$_3$): δ=84.9 (quint, J=150 Hz, 1 F), 63.2 (d, J=150 Hz, 4 F) ppm.

1,4-Bis(pentafluorosulfanyl)biphenyl (14)

(Kirsch, et al., *Angew. Chem.* 1999, 111, 2174; Kirsch, et al., *Angew. Chem. Int. Ed.* 1999, 38, 1989-1992) Palladium (II) acetate (0.3 mg, 0.001 mmol) was added to a solution of 1 (14.5 mg, 0.0384 mmol) in 0.15 g of methanol. The reaction mixture was stirred at 70° C. for 5.5 h and filtered through a pad of SiO$_2$ with the help of hexane. Removal of the solvent gave a colorless crystalline solid which was purified by SiO$_2$ column chromatography with hexane to give 14 (7.7 mg) as colorless crystals (99%); m.p. 196.0-197.0° C. (in sealed tube). IR (ATR): $\tilde{v}$=3007, 2992, 1599, 1481, 1391, 1277, 1260, 1101, 831, 810 cm$^{-1}$. MS (GC, EI): m/z=406 [M$^+$], 387 [M$^+$-F], 282, 190. $^1$H NMR (500 MHz, CDCl$_3$): δ=7.87 (d, J=8.6 Hz, 2H), 7.66 (d, J=8.6 Hz, 2H) ppm. $^{13}$C NMR (125 MHz, CDCl$_3$): δ=153.7 (C), 142.3 (C), 127.6 (2CH), 126.7 (2CH) ppm. $^{19}$F NMR (470 MHz, CDCl$_3$): δ=84.0 (quint, J=150 Hz, 1 F), 63.0 (d, J=150 Hz, 4 F) ppm.

1-(Pentafluorosulfanyl)-4-(phenylethynyl)benzene (24a)

(Bowden, et al., *Tetrahedron* 2000, 56, 3393-3408) Diazonium salt 1 (11.7 mg, 0.0368 mmol) was added to a mixture of phenylacetylene (11.4 mg, 0.0805 mmol), sodium iodide (9.8 mg, 0.065 mmol), and Pd(OAc)2 (0.5 mg, 0.002 mmol) in 0.23 g of 95% ethanol. Then triethylamine (10.6 mg, 0.077 mmol) was added to the mixture. The reaction mixture was stirred at 70° C. for 22 h, then filtered through a pad of SiO$_2$ with the help of hexane. Removal of the solvent gave a pale yellow crystalline solid which were purified by SiO$_2$ column chromatography with hexane to give 24a as a colorless oil (1.0 mg; 9%); m.p. 88.0-89.0° C. IR (ATR): $\tilde{v}$=2926, 2222, 1603, 1503, 1445, 1402, 1094, 835 cm$^{-1}$. MS (GC, EI): m/z=304 [M$^+$], 196. $^1$H NMR (500 MHz, CDCl$_3$): δ=7.74 (d, J=9.0 Hz, 2H), 7.60 (d, J=9.0 Hz, 2H), 7.55 (m, 2H), 7.39-7.37 (m, 3H) ppm. $^{13}$C NMR (125 MHz, CDCl$_3$): δ=153.0 (C), 131.8 (2CH), 131.6 (2CH), 129.0 (CH), 128.5 (2CH), 127.0 (C), 126.0 (2CH), 122.2 (C), 92.2 (C), 87.2 (C) ppm. $^{19}$F NMR (470 MHz, CDCl$_3$): δ=84.0 (quint, J=150 Hz, 1 F), 62.7 (d, J=150 Hz, 4 F) ppm.

1-(Pentafluorosulfanyl)-4-[(2-trifluoromethyl)phenylethynyl]benzene (24b)

Sodium iodide (9.8 mg, 0.065 mmol) was added portionwise to a solution of 1 (10.4 mg, 0.0327 mmol) in 0.17 g of 95% ethanol. To the mixture, triethylamine (7.8 mg, 0.077 mmol), (2-trifluoromethyl)phenylacetylene (13.7 mg, 0.0805 mmol), and Pd(OAc)$_2$ (0.5 mg, 0.002 mmol) were subsequently added. The reaction mixture was stirred at 70° C. for 4 h, then filtered through a pad of SiO$_2$ with the help of hexane. Removal of the solvent gave a brown oil which was purified by SiO$_2$ column chromatography with hexane to give 24b as a colorless oil (1.8 mg; 15%): IR (ATR): $\tilde{v}$=2232, 1605, 1503, 1323, 1261, 1175, 1134, 1111, 829 cm−1. MS (GC, EI): m/z=372 [M+], 353 [M+-F], 264, 243. 1H NMR (500 MHz, CDCl3): δ=7.76 (d, J=8.4 Hz, 2H), 7.72 (d, J=7.8 Hz, 1H), 7.70 (d, J=7.8 Hz, 1H), 7.62 (d, J=8.4 Hz, 6H), 7.56 (t, J=7.8 Hz, 1H), 7.48 (t, J=7.8 Hz, 1H) ppm. 13C NMR (125 MHz, CDCl3): δ=153.5 (C), 133.9 (C), 131.8 (q, J=34 Hz, C), 131.7 (2CH), 131.5 (CH), 128.7 (CH), 126.4 (C), 126.1 (3CH), 123.4 (q, J=274 Hz, C), 120.5 (C), 92.5 (C), 88.1 (C) ppm. 19F NMR (470 MHz, CDCl3): δ=83.8 (quint, J=150 Hz, 1 F), 62.6 (d, J=150 Hz, 4 F), −62.3 (s, 3 F) ppm.

1-(Pentafluorosulfanyl)-4-[(3,5-trifluoromethyl)phenylethynyl]benzene (24c)

Sodium iodide (9.3 mg, 0.062 mmol) was added portionwise to a solution of 1 (15.4 mg, 0.0484 mmol) in 0.15 g of 95% ethanol. To the mixture, triethylamine (10.0 mg, 0.0988 mmol), 3,5-di(trifluoromethyl)phenylacetylene (15.1 mg, 0.0634 mmol), and Pd(OAc)$_2$ (0.3 mg, 0.001 mmol) were subsequently added. The reaction mixture was stirred at 70° C. for 4 h, then filtered through a pad of SiO$_2$ with the help of hexane. Removal of solvent gave a brown oil which was purified by SiO$_2$ column chromatography with hexane to give 24c as a colorless oil (3.6 mg; 17%): IR (ATR): $\tilde{v}$=2231, 1615, 1599, 1498, 1387, 1279, 1180, 1138, 833 cm$^{-1}$. MS (GC, EI): m/z=440 [M$^+$], 421 [M$^+$-F], 332. $^1$H NMR (500 MHz, CDCl$_3$): δ=7.99 (s, 2H), 7.87 (s, 1H), 7.79 (d, J=8.7 Hz, 2H), 7.64 (d, J=8.7 Hz, 2H) ppm. $^{13}$C NMR (125 MHz, CDCl$_3$): δ=153.8 (C), 132.1 (q, J=34 Hz, 2 C), 131.9 (2CH), 131.6 (2CH), 126.3 (2CH), 125.5 (C), 124.7 (C), 122.8 (q, J=273 Hz, C), 122.3 (CH), 90.4 (C), 88.8 (C) ppm. $^{19}$F NMR (470 MHz, CDCl$_3$): δ=83.4 (quint, J=150 Hz, 1 F), 62.6 (d, J=150 Hz, 4 F), −63.1 (s, 6 F) ppm.

4-(Pentafluorosulfanyl)phenyl Azide (25a)

(Sheppard, *J. Am. Chem. Soc.* 1962, 84, 3064-3072) Trimethylsilyl azide (6.5 mg, 0.056 mmol) was added to a solution of 1 (10.2 mg, 0.0321 mmol) in [BMIM][BF$_4$] (65.0 mg). After stirring for 5 min, the mixture was extracted with hexane (0.5 mL×3) and the combined extracts was evaporated to give pure 25a as a colorless oil (6.8 mg, 86%): IR (ATR): ṽ=2124, 2099, 1586, 1501, 1287, 843 cm$^{-1}$. MS (GC, EI): m/z=245 [M$^+$], 219 [M$^+$-CN], 200 [M$^+$-CFN], 111. $^1$H NMR (500 MHz, CDCl$_3$): δ=7.74 (d, J=9.0 Hz, 2H), 7.08 (d, J=9.0 Hz, 2H) ppm. $^{13}$C NMR (125 MHz, CDCl$_3$): δ=150.3 (C), 143.3 (C), 127.7 (2CH), 118.9 (2CH) ppm. $^{19}$F NMR (470 MHz, CDCl$_3$): δ=84.4 (quint, J=150 Hz, 1 F), 63.5 (d, J=150 Hz, 4 F) ppm.

1-Iodo-4-(pentafluorosulfanyl)benzene 25b (Bowden, et al., *Tetrahedron* 2000, 56, 3393-3408) Trimethylsilyl iodide (15.0 mg, 0.0750 mmol) was added to a solution of 1 (11.0 mg, 0.0346 mmol) in [BMIM][BF$_4$] (67.6 mg). After stirring for 5 min the mixture was extracted with hexane (0.5 mL×3) and the combined extracts was evaporated to give pure 25b as a colorless oil (4.6 mg, 40%): MS (GC, EI): m/z=330 [M+], 311 [M$^+$ F], 222, 96. $^1$H NMR (500 MHz, CDCl$_3$): δ=7.82 (d, J=8.8 Hz, 2H), 7.48 (d, J=8.8 Hz, 2H) ppm. $^{13}$C NMR (125 MHz, CDCl$_3$): δ=137.9 (2CH), 127.5 (2CH), 98.2 (C) ppm. $^{19}$F NMR (470 MHz, CDCl3): δ=83.5 (quint, J=151 Hz, 1 F), 62.8 (d, J=151 Hz, 4 F) ppm.

4-(Pentafluorosulfanyl)phenyl Thiocyanate (25c)

A solution of ammonium thiocyanate (7.3 mg, 0.096 mmol) and 1 (10.1 mg, 0.0318 mmol) in 0.29 g of MeCN was heated at 70° C. for 0.5 h. After cooling, the mixture was filtered through SiO$_2$ with CH$_2$Cl$_2$ and the solvent was evaporated to give a pale yellow oil, whose purification by SiO$_2$ column chromatography with 9:1 hexane/CH$_2$Cl$_2$ furnished pure 25c as colorless crystals (2.6 mg, 31%); m.p. 67.2-68.2° C. IR (ATR): ṽ=3103, 2162, 1585, 1479, 1402, 1105, 1082, 837 cm−1. MS (GC, EI): m/z=261 [M$^+$], 242 [M$^+$-F], 153, 133. $^1$H NMR (500 MHz, CDCl$_3$): δ=7.84 (d, J=8.8 Hz, 2H), 7.61 (d, J=8.8 Hz, 2H) ppm. $^{13}$C NMR (125 MHz, CDCl$_3$): δ=154.0 (C), 129.6 (C), 128.7 (2CH), 127.8 (2CH), 108.6 (C) ppm. 19F NMR (470 MHz, CDCl$_3$): δ=82.5 (quint, J=151 Hz, 1 F), 62.9 (d, J=151 Hz, 4 F) ppm.

Reaction of 1 with TMSCl:

Trimethylsilyl chloride (6.0 mg, 0.055 mmol) was added to a solution of 1 (11.0 mg, 0.0346 mmol) in [BMIM][BF$_4$] (62.1 mg). After stirring for 2 d the mixture was extracted with hexane (0.5 mL×3) and the combined extracts was analyzed by GC-MS to show the formation of small amount of: 25d: (Sheppard, *J. Am. Chem. Soc.* 1962, 84, 3064-3072; Umemoto, et al., *Beilstein J. Org. Chem.* 2012, 8, 461-471) MS (GC, EI) m/z=238 and 240 (Mt), 221, 219, 132, 130.

Reaction of 1 with TMSBr:

Trimethylsilyl bromide (9.8 mg, 0.064 mmol) was added to a solution of 1 (10.0 mg, 0.0315 mmol) in [BMIM][BF$_4$] (57.4 mg). After stirring for 3 d the mixture was extracted with hexane (0.5 mL×3) and the combined extracts was analyzed by GC-MS to show the formation of 25e. The removal of the solvent gave as 25e (Sheppard, *J. Am. Chem. Soc.* 1962, 84, 3064-3072; Zarantonello, et al., *J. Fluorine Chem.* 2007, 128, 1449-1453; Welch & Lim, *Bioorg. Med. Chem.* 2007, 15, 6659-6666) as a colorless oil (0.5 mg, 6%).

Reaction of 1 with TMSCN/KF:

Trimethylsilyl cyanide (10.8 mg, 0.109 mmol) and KF (3.5 mg, 0.060 mmol) were added to a solution of 1 (10.7 mg, 0.0337 mmol) in [BMIM][BF$_4$] (55.0 mg). After stirring for 2 d the mixture was extracted with hexane (0.5 mL×3) and the combined extracts was analyzed by GC-MS to show the formation of small amount of 25f: MS (GC, EI): m/z=229 [M$^+$], 210 [M$^+$-F], 121.

1-(4-Pentafluorosulfanyl)phenyl-4-phenyl-1H-1,2,3-triazole (26a)

Cu—Zn (60/40) alloy nanopowder (<150 nm) (5.2 mg) was added into a solution of 25c (7.2 mg, 0.033 mmol) and phenylethyne (9.2 mg, 0.090 mmol). The mixture was heated at 70° C. for 19 h, then cooled to room temp. and filtered through Celite with the help of CH$_2$Cl$_2$. Evaporation of solvent produced a pale yellow crystalline solid which was washed with hexane to give pale yellow crystals of pure 26a (4.0 mg, 39%). The hexane solution was evaporated to give a pale yellow oil which was purified by SiO$_2$ column chromatography with hexane/EtOAc (7:3) to furnish additional amounts of 26a (colorless crystals; 1.3 mg, 13%); m.p. 246.0-247.2° C. IR (ATR): ṽ=3123, 1596, 1504, 1483, 1458, 1436, 1410, 1230, 1101, 1089, 830 cm$^{-1}$. MS (GC, EI): m/z=347 [M$^+$], 319 [M$^+$-N$_2$], 211, 192, 165, 116, 90. $^1$H NMR (500 MHz, CDCl$_3$): δ=8.26 (s, 1H), 7.98 (d, J=9.8 Hz, 1H), 7.95 (d, J=9.8 Hz, 2H), 7.93 (d, J=7.3 Hz, 2H), 7.49 (t, J=7.3 Hz, 2H), 7.41 (t, J=7.3 Hz, 1H) ppm. $^1$H NMR (500 MHz, [D6]acetone): δ=9.30 (s, 1H), 8.28 (d, J=9.2 Hz, 1H), 8.20 (d, J=9.2 Hz, 2H), 8.03 (d, J=7.6 Hz, 2H), 7.52 (t, J=7.6 Hz, 2H), 7.43 (t, J=7.6 Hz, 1H) ppm. $^{13}$C NMR (125 MHz, [D6]acetone): δ=151.4 (C), 148.3 (C), 139.4 (C), 130.5 (C), 129.0 (2CH), 128.4 (CH), 128.0 (2CH), 125.6 (2CH), 120.3 (2CH), 118.9 (CH) ppm. $^{19}$F NMR (470 MHz, CDCl$_3$): δ=83.1 (quint, J=150 Hz, 1 F), 63.1 (d, J=150 Hz, 4 F) ppm. $^{19}$F NMR (470 MHz, [D6]acetone): δ=83.5 (quint, J=148 Hz, 1 F), 62.6 (d, J=148 Hz, 4 F) ppm.

1-(4-Pentafluorosulfanyl)phenyl-4-[2-(trifluoromethyl)phenyl]-1H-1,2,3-triazole (26b)

Cu—Zn (60/40) alloy nanopowder (<150 nm) (6.7 mg) was added to a solution of 25c (8.0 mg, 0.033 mmol) and [2-(trifluoromethyl)phenyl]ethyne (10.1 mg, 0.0591 mmol). The mixture was heated at 70° C. for 19 h, then cooled to room temp. and filtered through Celite using CH$_2$Cl$_2$. Removal of solvent gave a pale green oil, which was purified by SiO$_2$ column chromatography using hexane/EtOAc (8:2) to give 26b as colorless crystals (9.1 mg, 65%); m.p. 92.5-93.0° C. IR (ATR): ṽ=1601, 1515, 1409, 1315, 1177, 1125, 1036, 833 cm$^{-1}$. MS (GC, EI): m/z=415 [M$^+$], 396 [M$^+$-F], 387 [M$^+$-N$_2$], 368. $^1$H NMR (500 MHz, CDCl$_3$): δ=8.26 (s, 1H), 8.05 (d, J=7.8 Hz, 1H), 7.98 (d, J=9.4 Hz, 2H), 7.95 (d, J=9.4 Hz, 2H), 7.82 (d, J=7.8 Hz, 1H), 7.70 (t, J=7.6 Hz, 1H), 7.56 (t, J=7.6 Hz, 1H) ppm. $^{13}$C NMR (125 MHz, CDCl$_3$): δ=153.3 (C), 145.5 (C), 138.6 (C), 132.2 (CH), 131.7 (CH), 128.9 (CH), 128.5 (C), 128.0 (2CH), 127.4 (q, J=30 Hz, C), 126.3 (CH), 124.1 (q, J=274 Hz, C), 120.6 (CH), 120.3 (2CH) ppm. $^{19}$F NMR (470 MHz, CDCl$_3$): δ=83.0 (quint, J=150 Hz, 1 F), 63.1 (d, J=150 Hz, 4 F), −58.6 (s, 3 F) ppm.

1-(4-Pentafluorosulfanyl)phenyl-4-[3,5-bis(trifluoromethyl)phenyl]-1H-1,2,3-triazole (26c)

Cu—Zn (60/40) alloy nanopowder (<150 nm) (6.9 mg) was added into a solution of 25c (5.5 mg, 0.022 mmol) and [3,5-bis(trifluoromethyl)phenyl]ethyne (10.2 mg, 0.0428 mmol). The mixture was heated at 70° C. for 19 h, then cooled to room temp. and filtered through Celite using $CH_2Cl_2$. Removal of the solvent gave a pale yellow oil, which was purified by $SiO_2$ column chromatography with hexane/EtOAc (8:2) to give 26c as colorless crystals (6.9 mg, 63%); m.p. 169.0-169.5° C. MS (GC, EI): m/z=483 [$M^+$], 464 [$M^+$-F], 455 [$M^+$ N2], 348, 328. IR (ATR): $\tilde{v}$=1669, 1601, 1514, 1373, 1330, 1278, 1177, 1134, 833 $cm^{-1}$. $^1H$ NMR (500 MHz, $CDCl_3$): δ=8.44 (s, 1H), 8.38 (s, 2H), 8.01 (d, J=9.3 Hz, 2H), 7.97 (d, J=9.3 Hz, 2H), 7.90 (s, 1H) ppm. $^{13}C$ NMR (125 MHz, $CDCl_3$): δ=153.7 (C), 146.3 (C), 138.4 (C), 132.5 (q, J=24 Hz, 2 C), 131.8 (C), 128.1 (2CH), 125.9 (2CH), 123.0 (q, J=273 Hz, 2 C), 122.2 (CH), 120.2 (2CH), 118.4 (CH) ppm. $^{19}F$ NMR (470 MHz, $CDCl_3$): δ=82.7 (quint, J=150 Hz, 1 F), 63.1 (d, J=150 Hz, 4 F), −63.0 (s, 6 F) ppm.

(E)-2,4-Dimethoxy-4'-(pentafluorosulfanyl)azobenzene (27a)

Diazonium salt 1 (9.8 mg, 0.030 mmol) in 1 mL of 95% aqueous ethanol was added to a solution of 1,3-dimethoxybenzene (8.7 mg, 0.063 mmol) in 0.5 mL of 95% aqueous ethanol. After 2 weeks, the solvent was evaporated to give a red oil, whose purification by $SiO_2$ column chromatography (1:1 hexane/$CH_2Cl_2$) afforded 27a as orange crystals (10.8 mg, 98%); m.p. 88.0-88.5° C. IR (ATR): $\tilde{v}$=2943, 1600, 1496, 1471, 1294, 1253, 1211, 767 $cm^{-1}$. MS (GC, EI): m/z=368 [$M^+$], 241 [$M^+$-$SF_5$], 165 [$M^+$-$C_6H_4SF_5$]. $^1H$ NMR (500 MHz, $CDCl_3$): δ=7.89 (d, J=9.0 Hz, 2H), 7.86 (d, J=9.0 Hz, 2H), 7.78 (d, J=9.0 Hz, 1H), 6.60 (d, J=2.4 Hz, 1H), 6.56 (dd, J=9.0, 2.4 Hz, 1H), 4.03 (s, 3H), 3.91 (s, 3H) ppm. $^{13}C$ NMR (125 MHz, $CDCl_3$): δ=164.8 (C), 159.5 (C), 154.4 (C), 154.1 (C), 136.7 (C), 126.9 (2CH), 122.5 (2CH), 118.2 (CH), 105.9 (CH), 98.9 (CH), 56.3 ($CH_3$), 55.7 ($CH_3$) ppm. $^{19}F$ NMR (470 MHz, $CDCl_3$): δ=84.3 (quint, J=150 Hz, 1 F), 63.2 (d, J=150 Hz, 4 F) ppm.

(E)-2,4,6-Trimethoxy-4'-(pentafluorosulfanyl)azobenzene (27b)

Diazonium salt 1 (11.9 mg, 0.0374 mmol) and 1,3,5-trimethoxybenzene (6.6 mg, 0.039 mmol) were dissolved in 0.18 g of 95% aqueous ethanol. After 0.1 h, a red solid precipitated which was filtered. The red precipitate was purified by $SiO_2$ column chromatography (7:3 hexane/ethyl acetate) to afford 27b as a red oil (11.2 mg, 75%): IR (ATR): $\tilde{v}$=2943, 1599, 1456, 1335, 1207, 1151, 1126, 837 $cm^{-1}$. MS (GC, EI): m/z=398 [$M^+$], 271 [$M^+$-$SF_5$], 195, 152. $^1H$ NMR (500 MHz, $CDCl_3$): δ=7.91 (d, J=9.3 Hz, 2H), 7.85 (d, J=9.3 Hz, 2H), 6.23 (s, 2H), 3.93 (s, 6H), 3.92 (s, 3H) ppm. $^{13}C$ NMR (125 MHz, $CDCl_3$): δ=164.4 (C), 156.4 (2 C), 154.6 (C), 153.9 (C), 127.1 (C), 126.9 (2CH), 122.0 (2CH), 91.4 (2CH), 56.6 (2$CH_3$), 55.7 ($CH_3$) ppm. $^{19}F$ NMR (470 MHz, $CDCl_3$): δ=84.5 (quint, J=150 Hz, 1 F), 63.3 (d, J=150 Hz, 4 F) ppm.

(E)-2,4,5-Trimethoxy-4'-(pentafluorosulfanyl)azobenzene (27c)

Diazonium salt 1 (14.1 mg, 0.0443 mmol) and 1,2,4-trimethoxybenzene (15.6 mg, 0.0928 mmol) were dissolved in 0.148 g of 95% aqueous ethanol. After 0.1 h, a red solid precipitated. After filtration the red solid was purified by $SiO_2$ column chromatography (7:3 hexane/ethyl acetate) to give 27c as a red oil (12.8 mg, 72%): IR (ATR): $\tilde{v}$=2941, 1607, 1598, 1505, 1472, 1436, 1269, 1209, 1126, 1093, 1030, 839, 824 $cm^{-1}$. MS (GC, EI): m/z=398 [$M^+$], 140, 110. $^1H$ NMR (500 MHz, $CDCl_3$): δ=7.91 (d, J=9.0 Hz, 2H), 7.86 (d, J=9.0 Hz, 2H), 7.44 (s, 1H), 6.64 (s, 1H), 4.07 (s, 3H), 4.01 (s, 3H), 3.93 (s, 3H) ppm. $^{13}C$ NMR (125 MHz, $CDCl_3$): δ=154.74 (C), 154.70 (C), 154.3 (C), 154.0 (C), 144.1 (C), 135.1 (C), 126.9 (2CH), 122.4 (2CH), 98.8 (CH), 97.5 (CH), 57.6 ($CH_3$), 56.22 ($CH_3$), 56.17 (CH3) ppm. $^{19}F$ NMR (470 MHz, $CDCl_3$): δ=84.4 (quint, J=150 Hz, 1 F), 63.3 (d, J=150 Hz, 4 F) ppm.

(E)-4-Hydroxy-4'-(pentafluorosulfanyl)azobenzene (27d)

Diazonium salt 1 (11.6 mg, 0.0365 mmol), phenol (9.5 mg, 0.10 mmol), and sodium acetate (10.2 mg, 0.124 mmol) were dissolved in 0.21 g of acetonitrile. After 1 month, the solution was filtered through Celite 545. Evaporation of the solvent gave a red oil, which was purified by $SiO_2$ column chromatography (9:1 hexane/ethyl acetate) and following preparative TLC ($SiO_2$, $CH_2Cl_2$) afforded 27d as yellow-orange crystals (7.3 mg, 62%); m.p. 110.0-111.0° C. IR (ATR): $\tilde{v}$=3261, 1593, 1505, 1467, 1436, 1402, 1271, 1235, 1142, 1094, 829 $cm^{-1}$. MS (GC, EI): m/z=324 [$M^+$], 305 [$M^+$-F], 197, 121, 93, 65. $^1H$ NMR (500 MHz, $CDCl_3$): δ=7.92-7.88 (m, 6H), 6.97 (d, J=8.8 Hz, 2H), 5.50 (br. s, 1H) ppm. $^{13}C$ NMR (125 MHz, $CDCl_3$): δ=159.1 (C), 154.4 (C), 153.7 (C), 147.0 (C), 127.0 (2CH), 125.6 (2CH), 122.5 (2CH), 116.0 (2CH) ppm. $^{19}F$ NMR (470 MHz, $CDCl_3$): δ=84.1 (quint, J=150 Hz, 1 F), 63.2 (d, J=150 Hz, 4 F) ppm.

(E)-4-Amino-4'-(pentafluorosulfanyl)azobenzene (27e)

Diazonium salt 1 (11.1 mg, 0.0349 mmol) and aniline (32.0 mg, 0.344 mmol) were dissolved in 0.19 g of 95% ethanol. After 20 d, the solution was filtered through Celite 545. Evaporation of the solvent gave an orange oil, which was purified by $SiO_2$ column chromatography (8:2 hexane/ethyl acetate) and following preparative TLC ($SiO_2$, $CH_2Cl_2$) afforded 27e as orange crystals (2.5 mg, 22%); m.p. 153.0-154.5° C. IR (ATR): $\tilde{v}$=3417, 2915, 1666, 1628, 1603, 1507, 1398, 1302, 1148, 1092, 834 $cm^{-1}$. MS (GC, EI): m/z=323 [$M^+$], 197, 120, 94, 65. $^1H$ NMR (500 MHz, $CDCl_3$): δ=7.88-7.82 (m, 6H), 6.76 (d, J=8.8 Hz, 2H), 2.20 (br. s, 1H) ppm. $^{13}C$ NMR (125 MHz, $CDCl_3$): δ=154.1 (C), 150.5 (C), 145.3 (C), 126.9 (2CH), 125.8 (2CH), 122.2 (2CH), 114.5 (2CH) ppm. $^{19}F$ NMR (470 MHz, $CDCl_3$): δ=84.4 (quint, J=150 Hz, 1 F), 63.2 (d, J=150 Hz, 4 F) ppm.

2,4,6-Trimethyl-4'-(pentafluorosulfanyl)biphenyl (28a)

Sodium iodide (5.2 mg, 0.035 mmol) was added portionwise to a solution of 1 (10.4 mg, 0.0327 mmol) and mesitylene (33.6 mg, 0.280 mmol) in $CH_3CN$ (0.14 g). The reaction mixture was filtered through Celite 545 by using $CH_2Cl_2$. The solvent was evaporated to give pale-red oil. NMR analysis indicated the formation of a 2:1 mixture of 25b and 28a which were separated by $SiO_2$ column chromatography using hexane to give 25b as colorless crystals (6.5 mg, 60%) and 28a as colorless crystals (3.3 mg, 31%).

25b: $^1$H NMR (500 MHz, CDCl$_3$): δ=7.82 (d, J=8.8 Hz, 2H), 7.48 (d, J=8.8 Hz, 2H) ppm. $^{19}$F NMR (470 MHz, CDCl$_3$): δ=83.5 (quint, J=150 Hz, 1 F), 62.8 (d, J=150 Hz, 4 F) ppm.

28a: M.p. 121.8-122.8° C. MS (GC, EI): m/z=322 [M$^+$], 307 [M$^+$-CH3], 195 [M$^+$-SF5], 180 [M$^+$-CH$_3$SF$_5$]. IR (ATR): ṽ=2292, 1612, 1476, 1396, 1096, 765 cm$^{-1}$. 1H NMR (500 MHz, CDCl$_3$): δ=7.80 (d, J=8.6 Hz, 2H), 7.24 (d, J=8.6 Hz, 2H), 6.96 (s, 2H), 2.34 (s, 3H), 1.99 (s, 6H) ppm. $^{13}$C NMR (125 MHz, CDCl$_3$): δ=152.4 (C), 145.0 (C), 137.4 (C), 136.9 (2 C), 135.6 (2CH), 129.7 (2CH), 128.3 (2CH), 126.1 (2CH), 21.0 (CH3), 20.7 (2CH$_3$) ppm. $^{19}$F NMR (470 MHz, CDCl$_3$): δ=85.0 (quint, J=150 Hz, 1 F), 63.1 (d, J=150 Hz, 4 F) ppm.

2,5-Dimethyl-4'-(pentafluorosulfanyl)biphenyl (28b)

Sodium iodide (5.5 mg, 0.037 mmol) was added portion-wise to a solution of 1 (9.9 mg, 0.031 mmol) and p-xylene (60.1 mg, 0.566 mmol) in CH$_3$CN (0.11 g). The reaction mixture was filtered through Celite 545 using CH$_2$Cl$_2$. The solvent was evaporated to give a brown oil, which was purified by SiO$_2$ column chromatography with hexane to afford 25b (1.4 mg, 14%) and 28b as a colorless oil (1.3 mg, 14%): MS (GC, EI): m/z=308 [M$^+$], 181 [M$^+$-SF$_5$]. IR (ATR): ṽ=2924, 1599, 1493, 1456, 1395, 1099, 833 cm$^{-1}$. $^1$H NMR (500 MHz, CDCl$_3$): δ=7.79 (d, J=8.5 Hz, 2H), 7.40 (d, J=8.5 Hz, 2H), 7.18 (d, J=8.3 Hz, 1H), 7.12 (d, J=8.3 Hz, 1H), 7.02 (s, 1H), 2.36 (s, 3H), 2.22 (s, 3H) ppm. $^{13}$C NMR (125 MHz, CDCl$_3$): δ=155.0 (C), 145.6 (C), 139.5 (C), 132.0 (C), 130.5 (CH), 130.2 (CH), 129.4 (2CH), 128.8 (CH), 125.7 (2CH), 20.9 (CH$_3$), 19.8 (CH$_3$) ppm. $^{19}$F NMR (470 MHz, CDCl$_3$): δ=84.9 (quint, J=150 Hz, 1 F), 63.2 (d, J=150 Hz, 4 F) ppm.

2,3,5,6-Tetramethyl-4'-(pentafluorothio)biphenyl (28c)

NaI (5.7 mg, 0.038 mmol) was added portion-wise to a solution of 1 (12.0 mg, 0.0377 mmol) and 1,2,4,5-tetramethylbenzene (8.6 mg, 0.064 mmol) in CH$_3$CN (0.17 g). The reaction mixture was filtered through Celite 545 using CH$_2$Cl$_2$. The solvent was evaporated to give (a) a mixture containing 1,2,4,5-tetramethylbenzene and 25b (13.8 mg), and (b) the desired 28c as colorless crystals in very low yield (0.3 mg, 2%).

28c: M.p. 166.0-167.0° C. MS (GC, EI): m/z=336 [M$^+$], 321 [M$^{+-CH}$$_3$], 194 [M$^+$-CH$_3$SF$_5$]. IR (ATR): ṽ=2924, 2852, 1603, 1462, 1096, 843, 810 cm$^{-1}$. $^1$H NMR (500 MHz, CDCl3): δ=7.81 (d, J=8.7 Hz, 2H), 7.22 (d, J=8.7 Hz, 2H), 7.03 (s, 1H), 2.27 (s, 6H), 1.86 (s, 6H) ppm. $^{13}$C NMR (125 MHz, CDCl$_3$): δ=152.3 (C), 146.2 (C), 140.0 (C), 133.8 (2 C), 131.5 (2 C), 131.1 (CH), 129.7 (2CH), 126.0 (2CH), 20.1 (CH$_3$), 17.2 (CH$_3$) ppm. $^{19}$F NMR (470 MHz, CDCl$_3$): δ=85.0 (quint, J=150 Hz, 1 F), 63.2 (d, J=150 Hz, 4 F) ppm.

2-Methoxy-4'-(pentafluorosulfanyl)biphenyl,
3-Methoxy-4'-(pentafluorosulfanyl) biphenyl, and
4-Methoxy-4'-(pentafluorosulfanyl)biphenyl (28e)
(Isomer Mixture)

NaI (22.0 mg, 0.147 mmol) was added portion-wise to a solution of 1 (31.0 mg, 0.0974 mmol) and anisole (96.0 mg, 0.888 mmol) in CH$_3$CN (53.5 mg). The reaction mixture was neutralized with Na$_2$CO$_3$ and filtered through Celite 545 using hexane. The solvent was evaporated to give a pale yellow oil. Silica column chromatography with hexane afforded 25b (15.3 mg, 48%), 2-methoxy-4'-(pentafluorosulfanyl)biphenyl as colorless crystals (4.0 mg, 13%), 3-methoxy-4'-(pentafluorosulfanyl) biphenyl as a colorless oil (0.2 mg, 1%), a fraction containing both 3-methoxy-4'-(pentafluorosulfanyl)biphenyl and 4-methoxy-4'-(pentafluorosulfanyl)biphenyl (1:1) as colorless oil (2.0 mg, 7%), and 4-methoxy-4'-(pentafluorosulfanyl)biphenyl as colorless crystals (0.7 mg, 2%).

2-Methoxy-4'-(pentafluorosulfanyl)biphenyl (ortho)

Colorless crystals; m.p. 80.5-81.5° C. IR (ATR): ṽ=2944, 2841, 1601, 1485, 1400, 1264, 1244, 831 cm$^{-1}$. MS (GC, EI): m/z=310 [M$^+$], 291 [M$^+$-F], 204, 168, 139. $^1$H NMR (500 MHz, CDCl$_3$): δ=7.78 (d, J=8.8 Hz, 2H), 7.61 (d, J=8.8 Hz, 2H), 7.38 (td, J=7.8, 1.7 Hz, 1H), 7.30 (dd, J=7.5, 1.7 Hz, 1H), 7.06 (td, J=8.5, 1.0 Hz, 1H) 7.01 (d, J=8.3 Hz), 3.83 (s, 3H) ppm. $^{13}$C NMR (125 MHz, CDCl$_3$): δ=156.3 (C), 152.4 (C), 142.0 (C), 130.7 (C), 129.7 (3CH), 128.4 (CH), 125.6 (2CH), 121.0 (CH), 111.3 (CH), 55.5 (CH$_3$) ppm. $^{19}$F NMR (470 MHz, CDCl$_3$): δ=85.0 (quint, J=150 Hz, 1 F), 63.1 (d, J=150 Hz, 4 F) ppm.

3-Methoxy-4'-(pentafluorosulfanyl)biphenyl (meta)

Colorless oil. IR (ATR): ṽ=2916, 2849, 1740, 1599, 1572, 1487, 1463, 1397, 1224, 1102, 1030, 833 cm$^1$. MS (GC, EI): m/z=310 [M$^+$], 202, 172, 159, 154, 139. $^1$H NMR (500 MHz, CDCl$_3$): δ=7.82 (d, J=8.8 Hz, 2H), 7.65 (d, J=8.8 Hz, 2H), 7.40 (t, J=8.0 Hz, 1H), 7.17 (d, J=8.0 Hz, 1H), 7.10 (t, J=2.0 Hz, 1H), 6.96 (dd, J=8.0, 2.0 Hz, 1H), 3.88 (s, 3H) ppm. $^{13}$C NMR (125 MHz, CDCl$_3$): δ=160.0 (C), 152.9 (C), 144.4 (C), 140.5 (C), 130.1 (CH), 127.3 (2CH), 126.4 (2CH), 119.7 (CH), 113.6 (CH), 113.2 (CH), 55.4 (CH$_3$) ppm. $^{19}$F NMR (470 MHz, CDCl$_3$): δ=84.8 (quint, J=150 Hz, 1 F), 63.1 (d, J=150 Hz, 4 F) ppm.

4-Methoxy-4'-(pentafluorosulfanyl)biphenyl (para)

Colorless crystals; m.p. 102.0-104.0° C. IR (ATR): ṽ=2921, 2850, 1740, 1609, 1493, 1467, 1398, 1298, 1261, 1184, 1103, 1037, 830 cm$^{-1}$. MS (GC, EI): m/z=310 [M$^+$], 202, 187, 158, 139. $^1$H NMR (500 MHz, CDCl$_3$): δ=7.79 (d, J=8.8 Hz, 2H), 7.61 (d, J=8.8 Hz, 2H), 7.53 (d, J=8.8 Hz, 2H), 7.00 (d, J=8.8 Hz, 2H), 3.87 (s, 3H) ppm. $^{13}$C NMR (125 MHz, CDCl$_3$): δ=160.0 (C), 152.3 (C), 144.1 (C), 131.4 (C), 128.4 (2CH), 126.6 (2CH), 126.4 (2CH), 114.5 (2CH), 55.4 (CH$_3$) ppm. $^{19}$F NMR (470 MHz, CDCl$_3$): δ=85.0 (quint, J=150 Hz, 1 F), 63.2 (d, J=150 Hz, 4 F) ppm.

Solvolytic Dediazoniations i) In Methanol: Diazonium salt 1 (22.5 mg, 0.0314 mmol) was dissolved in methanol (0.82 mL). After 13 d stirring at room temp. a portion of the solution was diluted with CDCl$_3$ and analyzed by NMR, which indicated the formation of 1-fluoro-4-(pentafluorosulfanyl)benzene 30, (Umemoto, et al., *Beilstein J. Org. Chem.* 2012, 8, 461-471) 1-methoxy-4-(pentafluorosulfanyl)-benzene, (Beier, et al., *Org. Lett.* 2011, 13, 1466-1469) and 4-(pentafluorosulfanyl)phenol (Beier, et al., *Org. Lett.* 2011, 13, 1466-1469).

4-(Pentafluorosulfanyl)phenol

Pale-brown oil. MS (GC, EI): m/z=220 [M$^+$], 201 [M$^+$-F], 112, 84. $^1$H NMR (500 MHz, CDCl$_3$): δ=7.65 (d, J=8.9 Hz, 2H), 6.86 (d, J=8.9 Hz, 2H) ppm. $^{19}$F NMR (470 MHz, CDCl$_3$): δ=86.0 (quint, J=150 Hz, 1 F), 64.2 (d, J=150 Hz, 4 F) ppm.

ii) in 2,2,2-Trifluroethanol TFE: Diazonium salt 1 (24.1 mg, 0.0314 mmol) was dissolved in TFE (90.5 mg, 0.400 mmol) and the mixture was heated at 70° C. for 4 h. NMR analysis of the reaction mixture indicated the formation of 1-fluoro-4-(pentafluorosulfanyl)benzene (21), (Umemoto, et al., *Beilstein J. Org. Chem.* 2012, 8, 461-471) 1-(pentafluorosulfanyl)-4-(2,2,2-trifluoroethoxy)benzene (29), (Beier, et al., *Org. Lett.* 2011, 13, 1466-1469) and unreacted 1 in 39:56:5 ratio. Most of the solvent was evaporated to give a pale yellow oil, whose $SiO_2$ column chromatography with hexane/$CH_2Cl_2$ (9:1) afforded 29 as a colorless oil (6.6 mg, 29%): MS (GC, EI): m/z=302 [M$^+$], 283 [M$^+$-F]. IR (ATR): $\tilde{v}$=2951, 1593, 1504, 1288, 1248, 1163, 1103, 837 cm$^{-1}$. $^1$H NMR (500 MHz, CDCl$_3$): δ=7.74 (d, J=9.2 Hz, 2H), 6.98 (t, J=9.2 Hz, 2H), 4.40 (q, J=7.9 Hz, 2H) ppm. $^{13}$C NMR (125 MHz, CDCl$_3$): δ=158.8 (C), 148.1 (C), 128.0 (2CH), 122.9 (q, J=278 Hz, CF$_3$), 114.5 (2CH), 65.7 (q, J=36 Hz, CH$_2$) ppm. $^{19}$F NMR (470 MHz, CDCl$_3$): δ=85.0 (quint, J=150 Hz, 1 F), 64.0 (d, J=150 Hz, 4 F) ppm.

1-Fluoro-4-(pentafluorosulfanyl)benzene (30)

MS (GC, EI): m/z=222 [M$^+$], 203 [M$^+$-F]. $^1$H NMR (500 MHz, CDCl$_3$): δ=7.77 (dd, J=8.8, 4.7 Hz, 2H), 7.47 (t, J=8.8 Hz, 2H) ppm. $^{19}$F NMR (470 MHz, CDCl$_3$): δ=84.1 (quint, J=150 Hz, 1 F), 62.6 (d, J=150 Hz, 4 F), −107.1 (s, 1 F) ppm.

iii) In Triflic Acid: Diazonium salt 1 (7.1 mg, 0.022 mmol) was dissolved in TfOH (0.27 g) and the mixture was heated at 50° C. for 1 month. After cooling, a portion of the mixture was diluted with CDCl$_3$ and analyzed by NMR showing the formation of 4-(fluorosulfonyl)phenyl trifluoromethanesulfonate 31. The mixture was diluted with $CH_2Cl_2$, washed with 10% Na$_2$CO$_3$ aq. and dried with MgSO$_4$. Most of the solvent was evaporated to give a pale yellow oil, which was purified by $SiO_2$ column chromatography with hexane/$CH_2Cl_2$ (7:3) to afforded 31 as a colorless oil (6.9 mg, 100%). MS (GC, EI): m/z=308 [M$^+$], 289 [M$^+$-F]. IR (ATR): $\tilde{v}$=3107, 1587, 1486, 1418, 1213, 1136, 881 cm$^{-1}$. $^1$H NMR (500 MHz, CDCl$_3$): δ=8.16 (d, J=9.0 Hz, 2H), 7.57 (d, J=9.0 Hz, 2H) ppm. $^{13}$C NMR (125 MHz, CDCl$_3$): δ=153.9 (C), 133.2 (C), 131.2 (2CH), 123.0 (2CH). 19F NMR (470 MHz, CDCl$_3$): δ=66.6 (s, 1 F), −72.5 (s, 3 F) ppm.

iv) In 1,1,1,3,3,3-hexafluoro-2-propanol HFIP: Diazonium salt 1 (106.8 mg, 0.3359 mmol) was dissolved in HFIP (7.16 g) and the mixture was heated at 60° C. for 4 h. After cooling, Na$_2$CO$_3$ was added and the mixture was filtered. Most of the solvent was evaporated to give a pale-yellow oil, which was purified by SiO2 column chromatography with hexane/$CH_2Cl_2$ (9:1) to afford 1-(pentafluorosulfanyl)-4-[2,2,2-trifluoro-1-(trifluoromethyl)ethoxy]benzene (colorless oil; 2.0 mg, 1.6%), 1-fluoro-4-(fluorosulfonyl)benzene (Ferm & VanderWerf, *J. Am. Chem. Soc.* 1950, 72, 4809-4810) (colorless oil; 7.7 mg, 13%), and 2,2,2-trifluoro-1-(trifluoromethyl)-ethyl 4-fluorophenylsulfonate (Popov, et al., *Ukrainskii Khim. Zh.* 1991, 57, 843-849) (colorless oil; 15.7 mg, 14.3%). Elution with hexane/$CH_2Cl_2$ (8:2) gave 1-(fluorosulfonyl)-4-[2,2,2-trifluoro-1-(trifluoromethyl)ethoxy]benzene (colorless oil, 6.6 mg, 6.0%), a 2:1 mixture of 1-(fluorosulfonyl)-4-[2,2,2-trifluoro-1-(trifluoromethyl)ethoxy]benzene and 2,2,2-trifluoro-1-(trifluoromethyl)ethyl-4-[2,2,2-trifluoro-1-(trifluoromethyl)ethoxy]phenylsulfonate (colorless oil, 27.2 mg, 19.1%), and 4-[2,2,2-trifluoro-1-(trifluoromethyl)ethoxy]phenylsulfonate (colorless oil, 3.8 mg, 2.4%).

1-(Pentafluorothio)-4-[2,2,2-trifluoro-1-(trifluoromethyl)ethoxy]-benzene

Colorless oil. MS (GC, EI): m/z=370 [M$^+$], 361 [M$^+$-F], 262, 224, 111, 83. IR (ATR): $\tilde{v}$=1596, 1502, 1369, 1291, 1244, 1199, 1105, 846 cm$^{-1}$. $^1$H NMR (500 MHz, CDCl$_3$): δ=7.79 (d, J=9.1 Hz, 2H), 7.14 (d, J=9.1 Hz, 2H) ppm. $^{13}$C NMR (125 MHz, CDCl$_3$): δ=158.6 (C), 149.7 (C), 128.3 (2CH), 120.2 (q, J=285 Hz, 2 C), 116.6 (2CH), 75.4 (m, CH) ppm. $^{19}$F NMR (470 MHz, CDCl$_3$): δ=84.0 (quint, J=151 Hz, 1 F), 63.6 (d, J=151 Hz, 4 F), −73.4 (d, J=5 Hz, 6 F) ppm.

1-Fluoro-4-(fluorosulfonyl)benzene

Colorless oil. IR (ATR): $\tilde{v}$=1593, 1498, 1416, 1210, 836, 768 cm$^{-1}$. MS (GC, EI): m/z=178 [M$^+$], 159 [M$^+$-F], 111, 83, 75. $^1$H NMR (500 MHz, CDCl$_3$): δ=8.07 (dd, J=9.1, 4.9 Hz, 2H), 7.33 (t, J=8.4 Hz, 2H) ppm. $^{13}$C NMR (125 MHz, CDCl$_3$): δ=166.8 (d, J=260 Hz, C), 131.5 (d, J=10 Hz, 2CH), 129.0 (d, J=26 Hz, C), 117.2 (d, J=23 Hz, 2CH) ppm. $^{19}$F NMR (470 MHz, CDCl$_3$): δ=66.8 (s, 1 F), −99.3 (m, 1 F) ppm.

2,2,2-Trifluoro-1-(trifluoromethyl)ethyl 4-Fluorophenylsulfonate

Colorless oil. IR (ATR): $\tilde{v}$=1593, 1498, 1375, 1363, 1290, 1234, 1204, 1191, 1066, 880, 837, 793 cm$^{-1}$. MS (GC, EI): m/z=326 [M$^+$], 159, 111, 75. $^1$H NMR (500 MHz, CDCl$_3$): δ=7.98 (dd, J=8.9, 4.9 Hz, 2H), 7.30 (dd, J=8.9, 8.0 Hz, 2H), 5.28 (m, 1H) ppm. $^{13}$C NMR (125 MHz, CDCl$_3$): δ=166.6 (d, J=260 Hz, C), 131.2 (d, J=10 Hz, 2CH), 130.4 (d, J=3 Hz, C), 119.7 (q, J=284 Hz, 2 C), 117.1 (d, J=23 Hz, 2CH), 72.0 (m, C) ppm. $^{19}$F NMR (470 MHz, CDCl$_3$): δ=73.1 (d, J=6 Hz, 1 F), −100 (m, 1 F) ppm.

1-(Fluorosulfonyl)-4-[2,2,2-trifluoro-1-(trifluoromethyl)ethoxy]-benzene

Colorless oil. IR (ATR): $\tilde{v}$=1596, 1498, 1290, 1248, 1211, 1200, 1180, 1103, 900, 776 cm$^{-1}$. MS (GC, EI): m/z=326 [M$^+$], 307 [M$^+$-F], 259, 224, 92. $^1$H NMR (500 MHz, CDCl$_3$): δ=8.07 (d, J=8.9 Hz, 2H), 7.29 (d, J=8.9 Hz, 2H), 5.00 (m, 1H) ppm. $^{13}$C NMR (125 MHz, CDCl$_3$): δ=161.8 (C), 131.3 (2CH), 128.6 (d, J=29 Hz, C), 120.5 (q, J=279 Hz, 2 C), 117.4 (2CH), 74.8 (m, C) ppm. $^{19}$F NMR (470 MHz, CDCl$_3$): δ=66.8 (s, 1 F), −73.2 (d, J=6 Hz, 6 F) ppm.

2,2,2-Trifluoro-1-(trifluoromethyl)ethyl-4-[2,2,2-trifluoro-1-(trifluoromethyl) ethoxy]phenylsulfonate Colorless oil. IR (ATR): $\tilde{v}$=1589, 1496, 1375, 1291, 1240, 1198, 1175, 1104, 1065, 881, 798 cm$^{-1}$. MS (GC, EI): m/z=474 [M$^+$], 326, 307, 259, 243, 111. $^1$H NMR (500 MHz, CDCl$_3$): δ=7.99 (d, J=8.9 Hz, 2H), 7.27 (d, J=8.9 Hz, 2H), 5.29 (m, 1H), 4.99 (m, 1H) ppm. $^{13}$C NMR (125 MHz, CDCl$_3$): δ=161.5 (C), 131.0 (2CH), 130.6 (C), 120.6 (q, J=283 Hz, C), 119.7 (q, J=280 Hz, C) 117.4 (2CH), 74.9 (m, C), 72.0 (m, C) ppm. 19F NMR (470 MHz, CDCl$_3$): δ=−73.1 (d, J=6 Hz, 6 F), −73.2 (d, J=6 Hz, 6 F) ppm.

v) In CF$_3$COOH (TFAH): Diazonium salt 1 (29.7 mg, 0.0934 mmol) was dissolved in TFAH (0.96 g) and the mixture was heated with 70° C. for 12 h. After cooling, a portion of the mixture was diluted with CDCl$_3$ and analyzed by NMR which indicated the formation of 1-fluoro-4-(pentafluorosulfanyl)benzene, (Umemoto, et al., *Beilstein J. Org. Chem.* 2012, 8, 461-471) 1-fluoro-4-(fluorosulfonyl)benzene, (Ferm & VanderWerf, *J. Am. Chem. Soc.* 1950, 72, 4809-4810) 4-(pentafluorosulfanyl)phenol, (Beier, et al., *Org. Lett.* 2011, 13, 1466-1469) and 4-(fluorosulfonyl)phenol (Jackson & Mabury, *Environ. Toxicol. Chem.* 2009, 28, 1866-1873; Steinkopf, et al.,*J. Prakt. Chem.* 1927, 117, 1-82). Most of the solvent was evaporated to give a pale yellow oil, which was purified by SiO$_2$ column chromatography with hexane/EtOAc (9:1) to afford: 4-(pentafluorosulfanyl)phenol, 4-(fluorosulfonyl)phenol (colorless oil; 3.5 mg), and 4-(fluorosulfonyl)phenol (colorless oil; 2.4 mg, 15%).

4-(Fluorosulfonyl)phenol

Colorless oil. MS (GC, EI): m/z=176 [M$^+$], 157 [M$^+$-F], 109, 81, 65, 63. $^1$H NMR (500 MHz, CDCl$_3$): δ=7.91 (d, J=8.8 Hz, 2H), 7.02 (d, J=8.8 Hz, 2H), 2.89 (br. s, 1H) ppm. $^{13}$C NMR (125 MHz, CDCl$_3$): δ=161.9 (C), 131.2 (2CH), 131.1 (C), 116.4 (2CH) ppm. $^{19}$F NMR (470 MHz, CDCl$_3$): δ=67.2 (s, 1 F) ppm.

vi) In [BMIM][NTf2]: Diazaonium salt 1 (44.8 mg, 0.141 mmol) was dissolved in [BMIM][NTf$_2$] (0.4514 g, 1.076 mmol) and the mixture was heated at 70° C. for 15 h. NMR analysis of the reaction mixture indicated the formation of 34 and 35 and 30 in a 77:8:15 ratio. The mixture was extracted with hexane and the solvent was evaporated to give a pale yellow oil, whose SiO$_2$ column chromatography with hexane/CH$_2$Cl$_2$ (8:2) afforded 35 (colorless crystals; 2.0 mg, 3%) and 34 (colorless oil; 24.3 mg, 36%).

34: MS (GC, EI): m/z=483 [M$^+$], 464 [M$^+$-F]. IR (ATR): ṽ=1495, 1395, 1343, 1219, 1130, 1076, 839 cm$^{-1}$. $^1$H NMR (500 MHz, CDCl$_3$): δ=7.95 (d, J=9.1 Hz, 2H), 7.48 (t, J=9.1 Hz, 2H) ppm. $^{13}$C NMR (125 MHz, CDCl$_3$): δ=153.9 (C), 149.6 (C), 129.0 (2CH), 122.4 (2CH), 118.7 (q, J=221 Hz, CF$_3$), 118.6 (q, J=221 Hz, CF$_3$) ppm. $^{19}$F NMR (470 MHz, CDCl$_3$): δ=81.6 (quint, J=150 Hz, 1 F), 63.1 (d, J=150 Hz, 4 F), −72.5 (s, 3 F), −77.8 (s, 3 F) ppm.

35: Dec. 245.0° C. (in a sealed tube). MS (GC, EI): m/z=483 [M$^+$], 464 [M$^+$-F]. IR (ATR): ṽ=1449, 1232, 1219, 1117, 837 cm$^{-1}$. $^1$H NMR (500 MHz, CDCl3): δ=7.92 (d, J=8.7 Hz, 2H), 7.54 (t, J=8.7 Hz, 2H) ppm. $^{13}$C NMR (125 MHz, CDCl3): δ=154.7 (C), 134.4 (C), 131.6 (2CH), 127.9 (2CH), 121.7 (q, J=222 Hz, CF3) ppm. $^{19}$F NMR (470 MHz, CDCl3): δ=81.3 (quint, J=150 Hz, 1 F), 62.7 (d, J=150 Hz, 4 F), −70.4 (s, 6 F) ppm.

vii) In [BMIM][BF$_4$] and [BMIM][PF$_6$]: Diazonium salt 1 (10.1 mg, 0.0318 mmol) was dissolved in the IL (90 mg) and the mixture was heated to 70° C. in an oil bath for 8 h. NMR analysis of the reaction mixture indicated quantitative formation of fluoro derivative 30 (Umemoto, et al., *Beilstein J. Org. Chem.* 2012, 8, 461-471; Ferm & VanderWerf, *J. Am. Chem. Soc.* 1950, 72, 4809-4810).

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of synthesizing pentafluorosulfanyl diazonium salt and synthesizing various pentafluorosulfanyl compounds, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of synthesizing an aromatic diazonium salt bearing at least one pentafluorosulfanyl group, comprising:
   providing an aromatic precursor bearing at least one pentafluorosulfanyl group;
   subjecting the aromatic precursor to diazotization with tert-butyl nitrite, amyl nitrite, or alkyl nitrite and using boron trifluoride etherate, boron trifluoride dibutyl etherate, boron trifluoride tert-butyl methyl etherate, or boron trifluoride acetonitrile, boron trifluoride methanol, in anhydrous solvent below room temperature to form an SF5-aromatic diazonium salt; and
   isolating the aromatic diazonium salt bearing at least one pentafluorosulfanyl group, wherein the aromatic diazonium salt comprises:
   formula II,

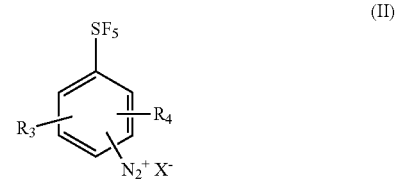

wherein R$_3$ is hydrogen an alkyl, or a diazonium;
   wherein R$_4$ is independently hydrogen or an alkyl;
   wherein X is BF$_4$; or
   formula III,

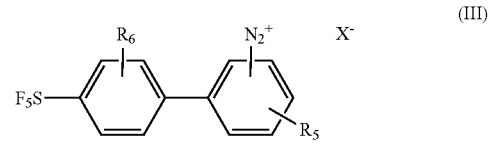

wherein R$_5$ is alkyl, or SF$_5$; and
   R$_6$ is hydrogen or diazonium.

2. The method of claim 1, further comprising purifying the aromatic diazonium salt with an acetonitrile/ether mixed solvent.

3. The method of claim 1, wherein the aromatic precursor is 1-pentafluorosulphanyl biphenyl-amine, 1,1'-bis-pentafluorosulphanyl-biphenyl-amine, 1,1'-bis-pentafluoro sulphanyl-biphenyl-diamine, or 1-pentafluorosulphanyl 3,5-diamine.

4. The method of claim 1, wherein the anhydrous solvent is dichloromethane, dichloroethane, chloroform or diethyl ether.

5. The method of claim 1, wherein the catalyst is boron trifluoride tert-butyl methyl etherate, boron trifluoride dibutyl etherate, or a boron trifluoride acetonitrile complex.

6. The method of claim 1 wherein the diazonium salt is isolated by the steps:
   dissolving the diazonium salt in minimal amount of acetonitrile to form a solution;
   adding an ethereal solvent until the diazonium salt precipitates from the solution,
      wherein the ethereal solution is acetonitrile/dibutyl ether, acetonitrile/dipropyl ether, acetonitrile/isopropyl ether, or acetonitrile/amyl ether;
   rinsing the salt precipitate with ether; and
   vacuum drying the salt precipitate.

7. The method of claim 6, wherein the salt precipitate is vacuum dried at room temperature.

8. The method of claim 1, wherein the aromatic precursor is subjected to BF3-amyl nitrite and an anhydrous solvent in an ice-bath.

* * * * *